United States Patent
Ouyang et al.

(10) Patent No.: US 11,254,685 B2
(45) Date of Patent: Feb. 22, 2022

(54) ABUSE-RESISTANT LONG-ACTING RELEASE OPIOID PRODRUGS

(71) Applicant: SUZHOU RUNXINDATAI PHARMACEUTICS LTD CO., Suzhou (CN)

(72) Inventors: Hui Ouyang, Irvine, CA (US); Yong Qiu, San Diego, CA (US)

(73) Assignee: SUZHOU RUNXINDATAI PHARMACEUTICS LTD CO., Suzhou (CN)

( * ) Notice: Subject to any disclaimer, the term of this patent is extended or adjusted under 35 U.S.C. 154(b) by 4 days.

(21) Appl. No.: 16/631,384

(22) PCT Filed: Jul. 19, 2018

(86) PCT No.: PCT/US2018/042880
§ 371 (c)(1),
(2) Date: Jan. 15, 2020

(87) PCT Pub. No.: WO2019/018638
PCT Pub. Date: Jan. 24, 2019

(65) Prior Publication Data
US 2020/0148694 A1     May 14, 2020

Related U.S. Application Data

(60) Provisional application No. 62/534,907, filed on Jul. 20, 2017.

(51) Int. Cl.
*C07D 489/08* (2006.01)
*A61K 31/485* (2006.01)
*A61K 45/06* (2006.01)

(52) U.S. Cl.
CPC ............ *C07D 489/08* (2013.01); *A61K 45/06* (2013.01)

(58) Field of Classification Search
CPC .. C07D 489/08; C07D 489/04; A61K 31/485; A61P 25/04
USPC ............................................ 546/45; 514/282
See application file for complete search history.

(56) References Cited

U.S. PATENT DOCUMENTS

| | | |
|---|---|---|
| 5,750,534 A | 5/1998 | Yoa-Pu et al. |
| 8,623,888 B2 | 1/2014 | Cantrell et al. |
| 2005/0080012 A1 | 4/2005 | Mickle et al. |
| 2006/0105046 A1 | 5/2006 | Bentley et al. |
| 2008/0045558 A1 | 2/2008 | Gant et al. |
| 2011/0015398 A1 | 1/2011 | Cantrell et al. |
| 2011/0237614 A1 | 9/2011 | Jude-Fishburn et al. |
| 2016/0151352 A1 | 6/2016 | Mickle et al. |

FOREIGN PATENT DOCUMENTS

| | | |
|---|---|---|
| WO | 2011/008636 A1 | 1/2011 |
| WO | 2016/086113 A1 | 6/2016 |

OTHER PUBLICATIONS

International Search Report for PCT/US2018/042880 dated Sep. 25, 2018, 3 pages.
Written Opinion of the ISA for PCT/US2018/042880 dated Sep. 25, 2018, 6 pages.
Jash et al., "Sugar Derivatives of Morphine: A New Window for the Development of Potent Anesthetic Drugs," Natural Products and Bioprospecting 5, 2015, pp. 111-127.
U.S. Appl. No. 17/423,339, filed Jan. 16, 2020, Ouyang.
I. V. Ukrainets et al., "Studies of 3-O-acyl derivatives of naloxone as its potential prodrugs", Chemistry of Heterocyclic Compounds, vol. 45, No. 4, Apr. 1, 2009 (Apr. 1, 2009), pp. 405-416.
Aswani Dutt Vadlapudi et al., "Targeted lipid based drug conjugates: A novel strategy for drug delivery", International Journal of Pharmaceutics. Elsevier, vol. 434. No. 1. (May 15, 2012). pp. 315-324. DOI: 10.1016/J.IJPHARM.2012.05.033.
Sung et al., "Delivery of Nalbuphine and Its Prodrugs Across Skin by Passive Diffusion and Iontophoresis", Journal of Controlled Release, 2000, vol. 67, pp. 1-8 (8 total pages).
PubChem-CID-72196195, Creation Date: Dec. 16, 2013, <https://pubchem.ncbi.nim.gov/compound/72196195>, 7 total pages.
PubChem-CID-5359272, Creation Date: Jun. 24, 2005, <https://pubchem.ncbi.nim.gov/compound/5359272>, 59 total pages.
PubChem-CID-5311304, Creation Date: Jun. 24, 2005, <https://pubchem.ncbi.nim.gov/compound/5311304>, 39 total pages.
PubChem-CID-73716901, Creation Date: May 22, 2014, <https://pubchem.ncbi.nim.gov/compound/73716901>, 7 total pages.

*Primary Examiner* — Charanjit Aulakh
(74) *Attorney, Agent, or Firm* — Nixon & Vanderhye P.C.

(57) ABSTRACT

There are provided, prodrugs of opioid and other controlled substance, having enhanced physical and chemical stability to resist tampering and to make long-acting release formulations, and pharmaceutically accepted salts and solvates thereof. There are also provided methods of using the disclosed compounds as abuse deterrent products.

21 Claims, 3 Drawing Sheets

ABUSE-RESISTANT LONG-ACTING RELEASE OPIOID PRODRUGS

CROSS REFERENCE TO RELATED APPLICATIONS

This application is the U.S. national phase of International Application No. PCT/US2018/042880 filed Jul. 19, 2018, which designated the U.S. and claims benefit of U.S. Provisional Application No. 62/534,907, filed on Jul. 20, 2017, the contents of each of which are incorporated herein by reference in its entirety.

FIELD OF INVENTION

In various embodiments, the present invention relates generally to abuse-resistant products to combat prescription drug abuse. For example, in some embodiments, the present invention relates to the preparation and application of abuse-resistant long-acting release opioid products.

BACKGROUND OF THE INVENTION

The abuse of prescription opioid drugs is 'epidemic' in the United States. Opioids abuse rates have quadrupled in the decade from 1990 to 2000 (See e.g., Passik S D et al. *Clin J Pain* 22(2):173-181 (2006)). Center for Disease Control and Prevention released statistic data indicating that the number of new opioid users increased by 104% between 2000 and 2010. In 2010, there were 2.4 million opioid abusers in the United States (Lembke A *N Engl J Med* 367:1580-1 (2012)). By 2007, Americans were using 80% of world's supply of all opioids and 99% of hydrocodone (Manchikanti, *Pain Physician* 10:399-424 (2007)).

The abuse of prescription opioid drugs is associated with heavy social and economic costs. Prescription opioids overdose is responsible for more deaths than cocaine and heroine combined (Jones C M et al. *JAMA* 309:657-9 (2013)). Since 2003, the number of deaths related to prescription opioid drugs has increased annually, rising to more than 16,000 in 2010 alone (Volkow N D et al. *The New England Journal of Medicine* 370 (22): 2063-2066 (2014)). In addition to causing significant morbidity and mortality, the abuse of prescription opioid drugs created severe burden on health care system. The average direct health care costs for opioid abusers is eight times higher than the average for non-abusers. The economic impact of prescription drug abuse is estimated to be $72.5 billion each year in health care costs alone.

Despite the heavy social and economic costs associated with the abuse of prescription opioid drugs, opioids are essential for improving the care and outcomes for the 100 million adults living with chronic pain in the United States. It is estimated that the cost of medical treatment and lost productivity associated with chronic pain is S560-635 billion annually (Institute of Medicine, See http://www.nap.edu/openbook.php?record_id=13172 (2011)). Opioid are widely accepted for the treatment of severe acute pain and chronic pain in cancer patients. According to "Clinical Guidelines for the Use of Chronic Opioid Therapy in Chronic Noncancer Pain" by American Pain Society, opioids are also recommended for moderate or severe chronic noncancer pain if the condition 'is having an adverse impact on function or quality of life, and potential therapeutic benefits outweigh or are likely to outweigh potential harms'. The major risk factors of chronic opioid treatment are abuse, addiction, and diversion (Chou R et al, *J Pain.* 10(2):113-30 (2009)).

Extended-release (ER) opioid formulations have limited success in reducing the drug abuse risk during chronic pain treatment. Drug abusers seek to achieve euphoria by creating a "dump" effect, i.e., taking an excess number of pills orally or snorting, smoking, or injecting an altered formulation. The effect results in a much higher peak blood concentration ($C_{max}$) over a shorter period of time ($T_{max}$). The abuser's desired "reward" of euphoria can be measured by abuse quotient (AQ=$C_{max}/T_{max}$) (Raffa R B et al. *Drugs* 70(13): 1657-1675 (2010)). ER formulations seem a perfect solution to reduce the abuse quotient of prescription medicine by increasing $T_{max}$ and decreasing $C_{max}$. ER formulations also provide the convenience of long-acting effects for chronic pain management. FDA has approved numerous ER opioid products, such as Avinza, Exalgo, Kadian, MS Contin, Nucynta, Opana, and OxyContin. All these products employed various abuse-deterrent formulation technologies to deter drug abuse. However, when examined closely, ER formulations hold a greater attraction for abusers than immediate-release (IR) formulations because of their higher per-dose level of drug. Abusers can always crush, cut, break, chew, and extract the ER formulations. The altered formulation usually generates higher on-set blood concentration in a shorter period of time (Webster L. *Pain Med* 10 (S2): S124-S133 (2009)).

Adding deterrent chemical to opioid formulation is unsuccessful in reducing opioid abuse potential. One example is the addition of opioid receptor antagonist, naloxone or naltrexone, to decrease the user's response to drug effects when the user alters the formulation. Another example is the addition of niacin or acetaminophen in the opioid formulation to induce uncomfortable side effects when the user alters the formulation. Among the products, Suboxone is still on the market albeit playing a minor role. Other products, such as Embeda, Oxytrex, Oxecta, and Acuracet, either showed no evidence in reducing drug abuse potential, or encountered problems during product development process (Webster L R *Exp Opin Investig Drugs* 16(8): 1277-1283 (2007); Webster L R et al. *J Pain* 7(12):937-946 (2006); Largent-Milnes T M et al. *J Pain* 9(8):700-713 (2008)).

Prodrug strategy provides the potential to make abuse-resistant opioid products. Bio-MD technology involves the conjugation of peptide to opioid (Jenkins T E, et al, U.S. Pub. No. 2011/0262,355 A1). In the small intestine, peptide mask on the opioid is cleaved off by the enzyme trypsin to release the opioids. The inactive opioid conjugate is stable in systemic circulation following administration and is resistant to chemical manipulation until it is converted to active opioids in small intestine. Bio-MD technology is still in development stage.

In summary, formulation technology has led to limited success in developing abuse-deterrent opioid products. Prodrug technology provides a promising alternative in combatting prescription opioid drug abuse.

BRIEF SUMMARY OF THE INVENTION

In various embodiments, the present invention provides prodrugs for a controlled substance, such as opioid prodrugs, which can have physical, chemical and biological activities that resist/deter drug tampering and/or achieve long-acting release profile in vivo. The long-acting release profile makes it possible for doctors to use the opioid products only in hospital or doctor's office, limiting patents' access of the opioids outside the clinics and avoiding the potential of opioid abuse altogether.

Some embodiments of the present disclosure are directed to novel prodrugs of controlled substances e.g., as described herein. In some embodiments, the prodrug is a compound of Formula I-X or a pharmaceutically acceptable salt thereof, A-L-D                                    Formula I-X wherein A, L, and D are defined herein. In some embodiments, A is a residue of a lipid, a substituted lipid, a natural biodegradable polymer, or a synthetic biodegradable polymer. In some embodiments, D is a residue of a controlled substance (e.g., any of the compounds in Table 1, such as an opioid described herein, such as oxymorphone, hydromorphone, morphine, levorphanol, or oxycodone). L is typically a linker, such as an ester linker. Typically, administering the compound of Formula I-X can lead to release of the controlled substance or a metabolite thereof in vivo, e.g., through hydrolysis of the linker L.

In some specific embodiments, the novel prodrug is a prodrug of oxymorphone. In some embodiments, the prodrug is a compound of Formula 1, or a pharmaceutically acceptable salt thereof:

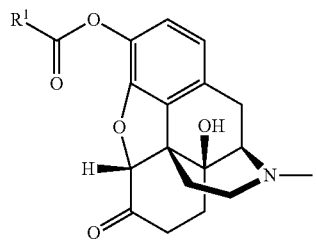

(Formula 1)

wherein $R^1$ is defined herein. In some embodiments, $R^1$ is an unsubstituted straight alkyl chain having 7-30 carbons. In some embodiments, $R^1$ is an unsubstituted branched alkyl chain having 7-30 carbons. In some embodiments, $R^1$ is a substituted or unsubstituted straight or branched alkyl chain having a total number of carbons of 7-30. In some embodiments, $R^1$ is an unsubstituted straight alkyl chain having a formula of $CH_3(CH_2)_n$—, wherein n is an integer of 8-24 (e.g., 10-24). In some specific embodiments, $R^1$ is selected from $CH_3(CH_2)_{10}$—, $CH_3(CH_2)_{12}$—, $CH_3(CH_2)_{14}$—, and $CH_3(CH_2)_{16}$—. In some embodiments, the novel prodrug is a prodrug of hydromorphone. In some embodiments, the prodrug is of Formula 2, or a pharmaceutically acceptable salt thereof:

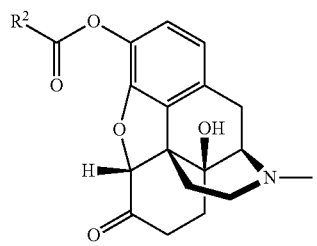

(Formula 2)

wherein $R^2$ is defined herein. In some embodiments, $R^2$ is an unsubstituted straight alkyl chain having 7-30 carbons. In some embodiments, $R^2$ is an unsubstituted branched alkyl chain having 7-30 carbons. In some embodiments, $R^2$ is a substituted or unsubstituted straight or branched alkyl chain having a total number of carbons of 7-30. In some embodiments, $R^2$ is an unsubstituted straight alkyl chain having a formula of $CH_3(CH_2)_n$—, wherein n is an integer of 8-24 (e.g., 10-24). In some specific embodiments, $R^2$ is selected from $CH_3(CH_2)_{10}$—, $CH_3(CH_2)_{12}$—, $CH_3(CH_2)_{14}$—, and $CH_3(CH_2)_{16}$—.

Certain embodiments of the present disclosure are directed to a pharmaceutical composition comprising the prodrugs herein. In some embodiments, the pharmaceutical composition is an abuse-deterrent formulation. In some embodiments, the pharmaceutical composition can comprise a compound of Formula I-X or a pharmaceutically acceptable salt thereof, A-L-D                                    Formula I-X wherein A, L, and D are defined herein. In some embodiments, the pharmaceutical composition can be formulated for injection, such as subcutaneous or intramuscular injection. In some embodiments, the pharmaceutical composition can be resistant towards (e.g., substantially stable under) common tampering conditions, such as baking soda or vinegar mediated hydrolysis at pH of about 8.3 or 2.4, respectively, or citric acid mediated hydrolysis at a pH of about 1.6. In some embodiments, the pharmaceutical composition comprising the compound of Formula I-X or pharmaceutically acceptable salt thereof can provide a long acting release of the controlled substance (e.g., oxymorphone or hydromorphone). In some embodiments, the pharmaceutical composition can, after administration, release the controlled substance, or a metabolite thereof, in a subject user over an extended period of time, such as at least 3 days. In some embodiments, the pharmaceutical composition comprises a compound of Formula I-X, or a pharmaceutically acceptable salt thereof, wherein D is a residue of morphine, oxymorphone, hydromorphone, levorphanol, or oxycodone. In some embodiments, the pharmaceutical composition comprises a compound of Formula 1 or 2 (e.g., any of the Compound Nos. 1-8), or a pharmaceutically acceptable salt thereof.

The prodrug herein can be a prodrug of an analgesic (e.g., oxymorphone or hydromorphone). Accordingly, certain embodiments of the present disclosure are also directed to methods of treating pain (e.g., chronic pain). In some embodiments, the method comprises administering to a subject in need thereof a therapeutically effective amount of the prodrug of an analgesic (e.g., oxymorphone or hydromorphone) or a pharmaceutically acceptable salt thereof, or a pharmaceutical composition (e.g., an injectable formulation) comprising the prodrug of the analgesic or pharmaceutically acceptable salt thereof. In some embodiments, the administering can be an injection, such as a subcutaneous or intramuscular injection. In some embodiments, the prodrug is a compound of Formula I-X, or a pharmaceutically acceptable salt thereof, wherein D is a residue of a controlled substance listed in Table 1 that is an analgesic, e.g., any of the opioid or phenolic opioid listed in Table 1. In some embodiments, D is a residue of morphine, oxymorphone, hydromorphone, levorphanol, or oxycodone. In some embodiments, the prodrug can be a compound of Formula 1 or 2 (e.g., any of the Compound Nos. 1-8), or a pharmaceutically acceptable salt thereof.

In some embodiments, the present disclosure also provides methods of reducing a likelihood of abuse of a controlled substance. In some embodiments, the method comprises providing a prodrug of the controlled substance, wherein the prodrug is a compound of Formula I-X (as defined herein) or a pharmaceutically acceptable salt thereof, wherein D in Formula I-X is a residue of the controlled substance, and formulating the prodrug in an abuse-deterrent formulation. In some embodiments, the abuse-deterrent formulation is an injectable formulation, such as a subcutaneous or intramuscular injectable formulation. In some embodiments, the abuse-deterrent formulation is resistant towards (e.g., substantially stable under) common tampering conditions, such as baking soda or vinegar mediated hydrolysis at pH of about 8.3 or 2.4, respectively, or citric acid mediated hydrolysis at a pH of about 1.6. In some embodiments, the abuse-deterrent formulation comprises micelles comprising the prodrug. In some embodiments, the method further comprising restricting the administration of the abuse-deterrent formulation to a hospital setting. In some embodiments, the abuse-deterrent formulation also provides a long acting release of the controlled substance. For example, the abuse-deterrent formulation can, after administration, release the controlled substance, or a metabolite thereof, in a subject user over an extended period of time, such as at least 3 days. In some embodiments, the prodrug is a compound of Formula I-X, or a pharmaceutically acceptable salt thereof, wherein D is a residue of a controlled substance listed in Table 1, e.g., any of the opioid or phenolic opioid listed in Table 1. In some embodiments, D is a residue of morphine, oxymorphone, hydromorphone, levorphanol, or oxycodone. In some embodiments, the prodrug can be a compound of Formula 1 or 2 (e.g., any of the Compound Nos. 1-8), or a pharmaceutically acceptable salt thereof.

In one aspect, the present invention provides a compound having the structure of Formula (I), or pharmaceutically accepted salt or solvate thereof:

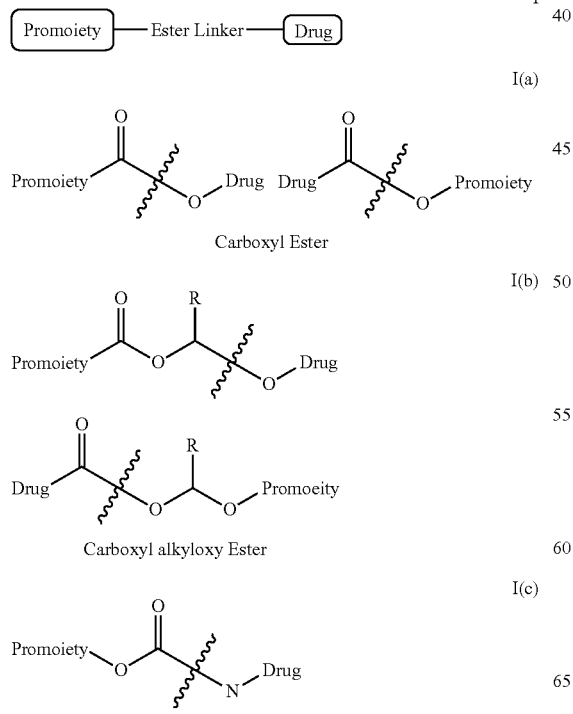

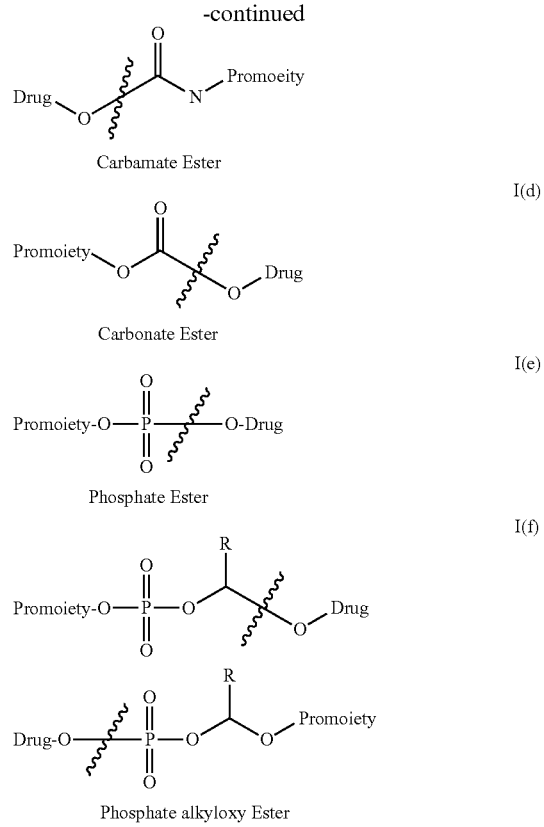

The compounds of Formula I are directed to opioid and other controlled substances (altogether defined as "drug") connected to a prodrug moiety (defined as "promoiety") by an ester linker as represented by Formula I. With reference to ester linker, it can be Formula I(a) as carboxyl ester; Formula I(b) as carboxylalkyloxy ester; Formula I(c) as carbamate ester; Formula I(d) carbonate ester; formula I(e) as phosphate ester; and I(f) as phosphate carboxylalkyloxy ester. Promoiety can be a lipid or natural biodegradable polymers or synthetic polymers. Drug can be selected from a Schedule II, III, or IV controlled substance with hydroxyl, secondary amine, or carboxyl acid group that is attached to the promoiety in Formula I via O, N, or CO of said hydroxyl, secondary amine, or carboxylic acid group. R is hydrogen, alkyl or substituted alkyl group. As used herein, the term "opioid" refers to, but is not limited to, opioid analogues as generally known in the arts. Any schedule II, III, or IV controlled substance as shown in Table 1 with a free hydroxyl group, secondary amine, or carboxylic acid group can be made into a prodrug as described in Formula (I).

In another aspect, there is provided a pharmaceutical composition which includes a compound of Formula (I) and a pharmaceutically acceptable excipient. In some embodiments, the pharmaceutical composition is formulated for injection, such as subcutaneous or intramuscular injection.

In another aspect, there is provided a method of resisting drug (e.g., opioid drug) tampering. In some embodiments, the method comprises formulating an effective amount of a compound of Formula (I) in an abuse deterrent form, thereby prevent drug abuse. In some embodiments, the compound of Formula (I) can also be formulated to achieve a long-acting release profile in vivo. The long-acting release profile makes it possible for doctors to use the opioid products only in hospital or doctor's office, limiting patents' access of the opioids outside the clinics and avoiding the potential of opioid abuse altogether.

DETAILED DESCRIPTION OF THE INVENTION

I. Definitions

Figure 1A:
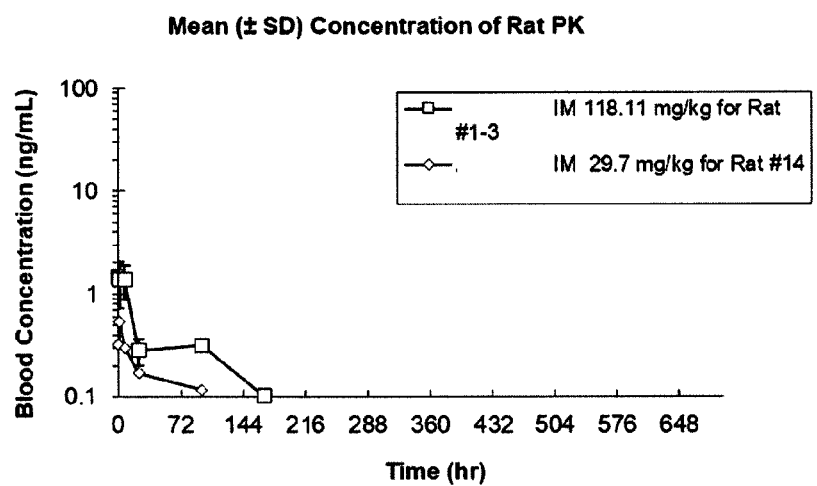
FIGS. 1A and 1B present graphs showing the plasma concentration profile of Compound 2 and oxymorphone, respectively, over the course of about 30 days post administration of Compound 2 in a rat pharmacokinetic (PK) study. The graphs were based on data points from mean (±Standard Deviation).

The abbreviations used herein have their conventional meaning within the chemical and biological arts.

Where moieties are specified by their conventional chemical formulae, written from left to right, they equally encompass the chemically identical moieties that would result from writing the structure from right to left, e.g., —$CH_2O$— is equivalent to —$OCH_2$—.

It is also meant to be understood that a specific embodiment of a variable moiety herein may be the same or different as another specific embodiment having the same identifier.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "substituted alkyl" means an alkyl group with carbon at any position connecting to a functional group. The functional group can be, but not limited to, alkoxy, alkylamino, alkylthio, heteroalkyl, cycloalkyl, heterocycloalkyl, halo, aryl, heteroalkyl, heteroatom ring heteroatom, or heteroaryl group.

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, including those groups having 10 or fewer carbon atoms. A "lower alkyl" or "lower alkylene" is a shorter chain alkyl or alkylene group, generally having eight or fewer carbon atoms.

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and a heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituent moieties for each of the above noted aryl and heteroaryl ring systems may be selected from the group of acceptable substituent moieties described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituent moieties for each type of radical are provided below.

Substituent moieties for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R, —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituent moieties, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituent moieties described for the alkyl radical, substituent moieties for the aryl and heteroaryl groups are varied and may be selected from, for example: halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituent moieties on adjacent atoms of the aryl or heteroaryl ring may optionally form a ring of the formula -Q'-C(O)—(CRR')$_q$-Q"-, wherein Q and Q" are independently —NR—, —O—, —CRR'— or a single bond, and q is an integer of from 0 to 3. Alternatively, two of the substituent moieties on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituent moieties on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituent moieties R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

Unless otherwise obvious from context, the term "controlled substance" as used herein refers to any of those defined in the United States Controlled Substances Act, 21 U.S.C. § 802, and includes any of the Schedule I, II, III, IV, and V drugs as listed in 21 U.S.C. § 812. See also 21 C.F.R. §§ 1308.11-15 for a list of controlled substances, the content of which is incorporated by reference in its entirety. The term "controlled substance" as used herein also includes any compound that can be converted into any of those defined in the United States Controlled Substances Act, 21 U.S.C. § 802, either in vitro or in vivo. Exemplified controlled substances are listed in Table 1 of the present disclosure.

The term "pharmaceutically acceptable salts" is meant to include salts of the compounds which are prepared with relatively nontoxic acids or bases, depending on the particular substituent moieties found on the compounds described herein. When prodrugs of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When prodrugs of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., 1977). Certain specific prodrugs of the present disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

As used herein, the term "prodrug(s) of the present disclosure" refers to any of the compounds described herein according to Formula I, I-X, 1, or 2, or any of Compound Nos. 1-8, isotopically labeled compound(s) thereof, possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt or base addition salt such as Na salt). Hydrates and solvates of the prodrugs of the present disclosure are considered compositions of the present disclosure, wherein the prodrug(s) is in association with water or solvent, respectively. Some of the prodrugs of the present disclosure can also exist in various polymorphic forms or amorphous forms. The prodrugs described herein include those compounds that readily undergo chemical changes under physiological conditions to provide the active compounds, i.e. opioids or other controlled substances. Additionally, prodrugs can be converted by chemical or biochemical methods in an ex vivo environment. For example, prodrugs can be slowly converted to the active compounds when placed in a transdermal patch reservoir with a suitable enzyme or chemical reagent.

Opioids are medications that relieve pain. They reduce the intensity of pain signals reaching the brain and affect those brain areas controlling emotion, which diminishes the effects of a painful stimulus. Medications that fall within this class include hydrocodone (e.g., Vicodin), oxycodone (e.g., OxyContin, Percocet), morphine (e.g., Kadian, Avinza), hydromorphone (e.g., Dilaudid, Palladone), codeine, and related drugs. Hydrocodone products are the most commonly prescribed for a variety of painful conditions, including dental and injury-related pain. Morphine is often used before and after surgical procedures to alleviate severe pain. Codeine, on the other hand, is often prescribed for mild pain. In addition to their pain relieving properties, some of these drugs—codeine and diphenoxylate (Lomotil) for example—can be used to relieve coughs and severe diarrhea.

Certain prodrugs of the present disclosure possess asymmetric carbon atoms (optical centers) or double bonds; the racemates, diastereomers, tautomers, geometric isomers and individual isomers are encompassed within the scope of the present invention. The prodrugs of the present disclosure do not include those which are known in the art to be too unstable to synthesize and/or isolate.

The prodrugs of the present disclosure may also contain unnatural proportions of atomic isotopes at one or more of the atoms that constitute such compounds. For example, the prodrugs of the present disclosure may be radiolabeled with radioactive isotopes, such as for example tritium ($^3$H), iodine-125 ($^{125}$I) or carbon-14 ($^{14}$C). All isotopic variations of the prodrugs of the present disclosure, whether radioactive or not, are encompassed within the scope of the present invention.

Solid and dashed wedge bonds indicate stereochemistry as customary in the art.

II. Compounds

In various embodiments, the present disclosure provides novel prodrugs of a controlled substance, pharmaceutical composition comprising the prodrug(s), and methods of preparing an abuse deterrent formulation comprising the prodrug(s), and methods of using the prodrug(s) or any of the pharmaceutical compositions, abuse deterrent formulations, for example for the treatment of pain, such as chronic pain.

The prodrugs of the present disclosure typically attach a controlled substance to a lipid or a polymer such as a natural biodegradable polymer or a synthetic biodegradable polymer. In some embodiments, the prodrug can be a compound of Formula I-X or a pharmaceutically acceptable salt thereof:

A-L-D             Formula I-X wherein

A is a residue of a lipid, a substituted lipid, a natural biodegradable polymer, or a synthetic biodegradable polymer;

D is a residue of a controlled substance (e.g., any of the compounds in Table 1, such as an opioid described herein, such as oxymorphone, hydromorphone, morphine, levorphanol, or oxycodone); and L is a linker of

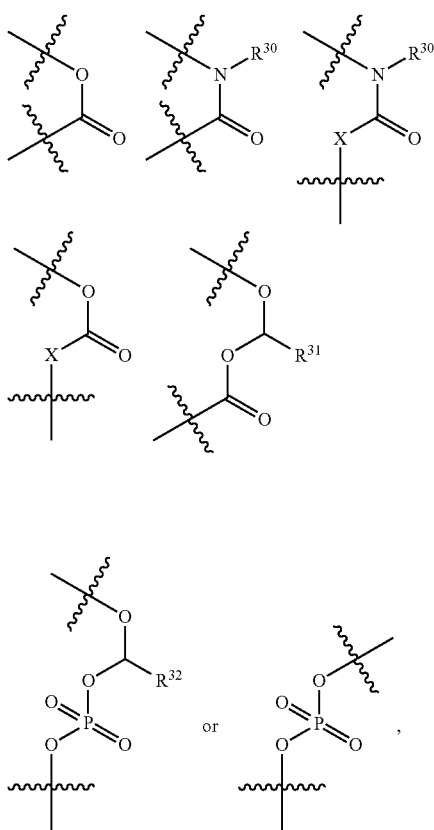

wherein X is O or NR$^{33}$, wherein R$^{30}$, R$^{31}$, R$^{32}$ and R$^{33}$ are each independently hydrogen, an alkyl, a substituted alkyl, an optionally substituted cycloalkyl, an optionally substituted heteroalkyl, an optionally substituted heterocycloalkyl, an optionally substituted aryl, or an optionally substituted heteroaryl, or R$^{30}$ or R$^{33}$ can be a bond attached to D when a cyclic —NH— function of the controlled substance forms part of the linker L. The linker L is typically derived from (but not necessarily) atoms/groups from the controlled substance and the lipid, substituted lipid, biodegradable polymer or synthetic polymer, with or without atoms/groups from another agent. In some embodiments, the controlled substance and the lipid, substituted lipid, biodegradable polymer or synthetic polymer are capable of forming the linker of L with or without another agent.

As used herein, the "residue" of a controlled substance should be understood as the remainder of the controlled substance, without the atom/group from which a part of the linker can be derived. For example, Scheme 1 shows a prodrug of hydromorphone, wherein a phenolic oxygen is attached to a carbonyl group, which represents the linker L, —C(=O)O—. Also, in that prodrug, D is a residue of hydromorphone, which is the remainder of hydromorphone without the phenolic hydroxyl group as shown in Scheme 1. The "residue" of the lipid, biodegradable polymer or synthetic polymer should be understood similarly. For example, as also shown in Scheme 1, in the prodrug of hydromorphone, A is a residue of palmitic acid, which is the remainder of palmitic acid without the COOH group. Typically, the compounds of Formula I-X (such as the prodrug of hydromorphone in Scheme 1) can be converted into the controlled substance, in vitro or in vivo, or otherwise, e.g., through hydrolysis of the linker L.

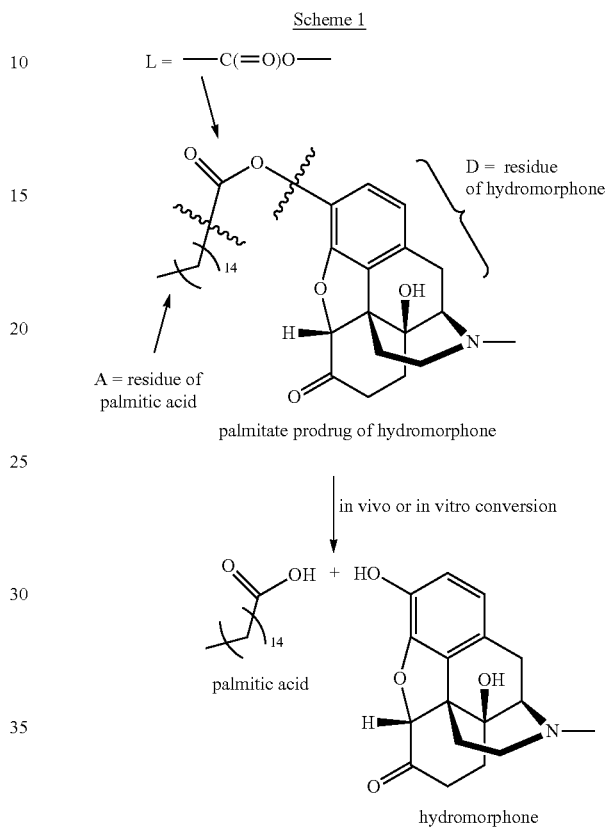

The variable D in Formula I-X can be a residue of various controlled substances. For example, in some embodiments, D can be a residue of a Schedule II, III or IV controlled substance, e.g., those described in Table 1. In some embodiments, D can be a residue of any of the controlled substance in Table 1, which has a hydroxyl, —NH— or —NH$_2$, or a carboxylic acid group, or a precursor thereof, wherein the oxygen or nitrogen atom, or the C(=O) group of the controlled substance can form part of the linker L in Formula I-X. The term "precursor" as used herein refers generally to a group or compound that can be converted into the referenced group or compound, typically with one or two chemical conversions. For example, a precursor of a hydroxyl, —NH— or —NH$_2$, or carboxylic acid group can be a group of O-Pg, N-Pg, N(Pg)(Pg') or C(=O)—Pg, wherein Pg and Pg' can be a protecting group. In some embodiments, D can be a residue of an opioid controlled substance, such as a phenolic opioid (i.e., an opioid that has a phenolic hydroxyl group, e.g., any phenolic opioid in Table 1, such as oxymorphone). In some embodiments, D can be a residue of a phenolic opioid, where D represents the remainder of the phenolic opioid without the phenolic hydroxyl group, see e.g., the residue of hydromorphone shown in Scheme 1. In some embodiments, D can be a residue of any opioid (e.g., any opioid in Table 1) with a hydroxyl, —NH— or —NH$_2$, or a carboxylic acid group, or a precursor thereof, wherein part of the linker L in Formula I-X can be derived from the hydroxyl, —NH— or —NH$_2$, or carboxylic acid group, or precursor thereof. For example, the linker can include the oxygen or nitrogen atom, or the C(=O) group of the opioid, e.g., in the form of an ester, amide bond, and the like, as described herein. In some embodiments, D can be a residue of morphine, oxymorphone, hydromorphone, levorphanol, or oxycodone. In controlled substances having two or more hydroxyl, —NH— or —NH$_2$, or carboxylic acid groups, the linker L can be derived from any of such groups. It should be noted that in some embodiments, D in Formula I-X can also be a residue of a controlled substance that has one or more of its hydroxyl, —NH— or —NH$_2$, and/or carboxylic acid groups, or a precursor thereof, attached to an independently selected residue A through a linker.

Residues of various lipids, substituted lipids, biodegradable natural or synthetic polymers are suitable for the compound of Formula I-X. For example, in some embodiments, A in Formula I-X can be a residue of a lipid. In some embodiments, A can be a residue of a lipid selected from saturated or unsaturated, straight chain or branched chain fatty acid with 7-30 carbons (not including the carbon from COOH), e.g., from eight (8) to twenty four (24) carbons, or from 10 to 24 carbons, which is optionally substituted; bile acids; squalene; vitamin E and its derivatives such as vitamin E TPGS (Tocopherol polyethylene glycol 1000 succinate); cholesterols; and retinoic acids. The number of carbons of residue A as referred to herein, unless otherwise specified or obvious from context, should be understood as the total number of carbons of residue A, including branched carbons and those from optional substituents. In some embodiments, A can be a residue of a straight chain saturated or unsaturated fatty acid, e.g., with 7-30 carbons (not including the carbon from COOH), such as with 8-24 carbons, or with 12-20 carbons, which is optionally substituted. In some embodiments, the fatty acid chain is unsubstituted. In some embodiments, the fatty acid chain is substituted, for example, one or more (e.g., 1, 2, 3, 4, 5, or 6) groups independently selected from halogen, optionally substituted alkyl (e.g., C$_{1-6}$ alkyl), optionally substituted heteroalkyl (e.g., C$_{1-6}$ heteroalkyl, e.g., with 1 or 2 heteroatoms independently selected from oxygen and nitrogen), optionally substituted alkenyl (e.g., C$_{2-6}$ alkenyl), optionally substituted alkynyl (e.g., C$_{2-6}$ alkynyl), optionally substituted cycloalkyl (e.g., C$_{3-6}$ cycloalkyl), optionally substituted aryl (e.g., C$_{6-14}$ aryl), optionally substituted heterocycloalkyl (e.g., 5-8 membered heterocycloalkyl), optionally substituted heteroaryl (e.g., 5-10 membered heteroaryl), short peptides (e.g. mono, di, tri, or tetra-peptides), —NR$^{100}$R$^{101}$, —C(=O)NR$^{100}$R$^{101}$, —COOR$^{102}$, and —OR$^{102}$, wherein R$^{100}$, R$^{101}$, and R$^{102}$ are each independently hydrogen, optionally substituted alkyl (e.g., C$_{1-6}$ alkyl), optionally substituted heteroalkyl (e.g., C$_{1-6}$ heteroalkyl, e.g., with 1 or 2 heteroatoms independently selected from oxygen and nitrogen), optionally substituted cycloalkyl (e.g., C$_{3-6}$ cycloalkyl), optionally substituted aryl (e.g., C$_{6-14}$ aryl), optionally substituted heterocycloalkyl (e.g., 5-8 membered heterocycloalkyl), optionally substituted heteroaryl (e.g., 5-10 membered heteroaryl), wherein each of the optionally substituted groups is independently optionally substituted with one or more (e.g., 1-3) substituents selected from oxo, halogen, hydroxyl, NH$_2$, —NH(C$_{1-4}$ alkyl), —N(C$_{1-4}$ alkyl)(C$_{1-4}$ alkyl), C$_{1-4}$ alkyl optionally substituted with 1-3 fluorine, C$_{1-4}$ alkoxy optionally substituted with 1-3 fluorine, C$_{2-4}$ alkenyl, C$_{2-4}$ alkynyl, C$_{3-6}$ cycloalkyl optionally substituted with 1-3 fluorine or 1-2 C$_{1-4}$ alkyl, and C$_{3-6}$ cycloalkoxy optionally substituted with 1-3 fluorine or 1-2 C$_{1-4}$ alkyl. As used herein, the short peptides as substituents can bond to the group which is substituted, e.g., the fatty acid chain, either through the N-terminal (e.g., through NH$_2$, optionally with one or both of the hydrogens substituted with C$_{1-4}$ alkyl or C$_{1-6}$ alkanoyl) or through the C-terminal (e.g., through —C(=O), —OC(=O), —NC(=O), etc.), with the non-connecting terminal being NH$_2$, or a protected derivative thereof such as N-Pg (e.g., NHC(=O)CH$_3$), in the case of N-terminal, or CO$_2$H, or ester (e.g., C$_{1-4}$ alkyl ester) or amide derivative thereof, in the case of C-terminal. In some embodiments, the short peptides as substituents can bond to the group which is substituted, e.g., the fatty acid chain, through the N-terminal. In some embodiments, the short peptides as substituents can bond to the group which is substituted, e.g., the fatty acid chain, through the C-terminal. In some embodiments, the short peptides can be a mono-, di-, tri-, or tetra-peptide, with 1, 2, 3 or 4 amino acid units, respectively, which can be derived from alpha-amino acids (e.g., D or L-amino acids) selected from alanine, isoleucine, leucine, methionine, valine, phenylalanine, tryptophan, tyrosine, asparagine, cysteine, glutamine, serine, threonine, aspartic acid, glutamic acid, arginine, histidine, lysine, glycine, and proline. In some embodiments, the fatty acid chain can be substituted with one or more (e.g., 1, 2, 3, 4, 5, or 6) independently chosen hydrophobic groups. As used herein, the term "hydrophobic group" generically refers to halogen or a carbon-containing group with 2 or less heteroatoms selected from oxygen and nitrogen atoms, which typically includes no OH or NH group and no basic nitrogen atom(s). Examples of hydrophobic groups include halogen, alkyl, alkoxy, alkenyl, alkynyl, cycloalkyl, cycloalkoxy, aryls, non-basic heterocycles and heteroaryls, etc. In some embodiments, the fatty acid chain is substituted with one or more (e.g., 1, 2, 3, 4, 5, or 6) groups independently chosen from halogen, C$_{1-4}$ alkyl, C$_{1-4}$ alkoxy, C$_{2-4}$ alkenyl, C$_{2-4}$ alkynyl, C$_{3-6}$ cycloalkyl, and C$_{3-6}$ cycloalkoxy. In some embodiments, A in Formula I-X has a formula of CH$_3$(CH$_2$)n-, wherein n can be an integer of 7-30 (e.g., 8-24 or 10-24). In some embodiments, A in Formula I-X can be a residue of a fatty acid having 1-6 double bonds.

In some embodiments, A in Formula I-X can also be a residue of a natural biodegradable polymer. For example, in some embodiments, A in Formula I-X can be a residue of a biodegradable polymer selected from alginate, chitosan, derived cellulose, starch, hyaluronic acid, and dextran. In some embodiments, A in Formula I-X can be a residue of a biodegradable polymer selected from peptides, polyesters, polyethers, polyurethanes, polyphosphazines, polycarbonates, and polyesteramide. In some embodiments, A in Formula I-X can also be a residue of a polymer selected from polylactic (PLA), polyglycolic (PGA), polycarprolactone (PCL), copolymers thereof, e.g., polylactic glycolic acid (PLGA); and polyethylene glycol (PEG) and its derivatives. The OH group, NH group or COOH group, or a precursor thereof, in the biodegradable polymer can form part of the linker L in Formula I-X, e.g., through an ester bond or an amide bond, etc. It should also be noted that in some embodiments, A in Formula I-X can also be a residue of a lipid, natural or synthetic biodegradable polymer that has one or more of its hydroxyl, —NH— or —NH$_2$, and/or carboxylic acid groups, or a precursor thereof, attached to an independently selected residue D through a linker.

The linker L in Formula I-X can vary depending on the attaching atoms/groups from the controlled substance and the lipid, biodegradable natural or synthetic polymer. For example, L can be an ester linker, amide linker, carbamate linker, carbonate linker, phosphonate linker, etc. In some embodiments, L can be

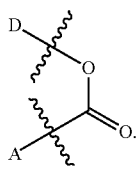

In some embodiments, L can be

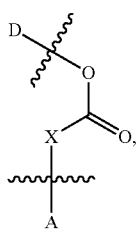

wherein X is O or NR$^{33}$, wherein R$^{33}$ is hydrogen, an alkyl (e.g., C1-4 alkyl) or a substituted alkyl (e.g., C1-4 alkyl optionally substituted with 1-3 substituents each independently oxo, F, hydroxyl, C$_{1-4}$ alkyl or C$_{1-4}$ alkoxy).

It should be noted that any of the definitions of D, A, or L described herein can be combined with any of the definitions of the others of D, A, and L as described herein. Such combinations are specifically contemplated and are within the scope of this invention.

In some embodiments, the prodrug can be a compound having the structure of Formula (I), or pharmaceutically accepted salt or solvate thereof:

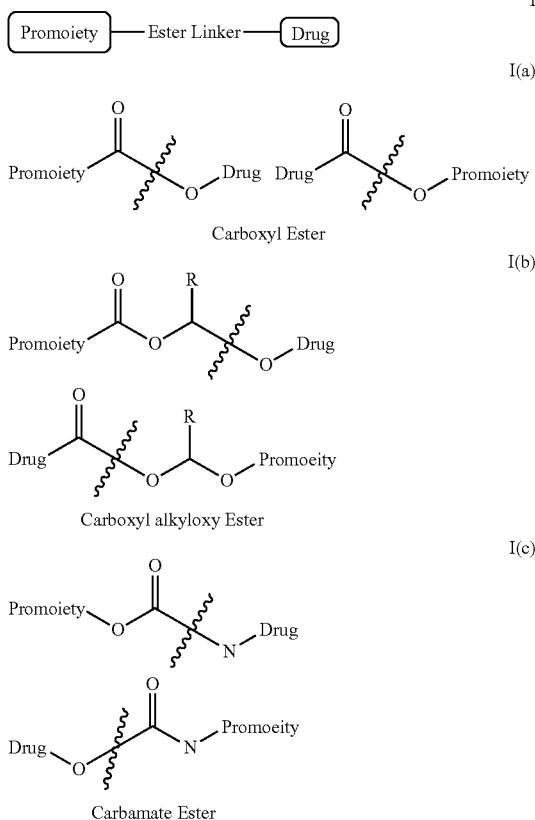

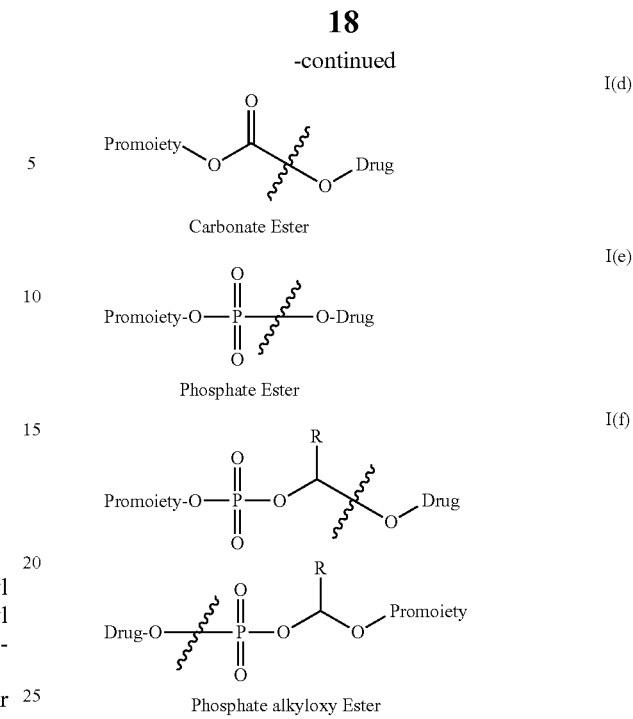

The compounds of Formula I are directed to opioid and other controlled substances (altogether defined as "drug" connected to a prodrug moiety (defined as "promoiety") by an ester linker as represented by Formula I. With reference to ester linker, it can be Formula I(a) as carboxyl ester; Formula I(b) as carboxylalkyloxy ester; Formula I(c) as carbamate ester; Formula I(d) carbonate ester; formula I(e) as phosphate ester; and I(f) as phosphate carboxylalkyloxy ester. Promoiety is a lipid or natural biodegradable polymers or synthetic polymers. Drug is selected from a Schedule II, III, or IV controlled substance with hydroxyl, secondary amine, or carboxyl acid group that is attached to the promoiety in Formula I via O, N, or CO of said hydroxyl, secondary amine, or carboxylic acid group. R is hydrogen, alkyl or substituted alkyl group. As used herein, the term "opioid" refers to, but is not limited to, opioid analogues as generally known in the arts. Any schedule II, III, or IV controlled substance as shown in Table 1 with a free hydroxyl group, secondary amine, or carboxylic acid group can be made into a prodrug as described in Formula (I).

In some specific embodiments, the present disclosure also provides a prodrug of oxymorphone. In some embodiments, the prodrug is a compound of Formula 1, or a pharmaceutically acceptable salt thereof

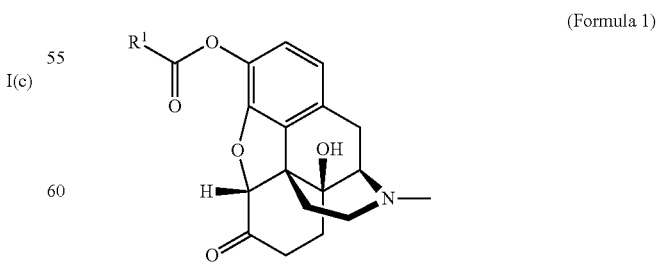

wherein R$^1$ is R$^{10}$, —OR$^{10}$, or —NHR$^{10}$, wherein R$^{10}$ is an optionally substituted straight or branched alkyl, alkenyl, or alkynyl chain having a total of 7-30 carbons. In some embodiments, the alkyl, alkenyl, or alkynyl chain is optionally substituted with one or more hydrophobic groups (e.g., described herein). In some embodiments, the alkyl, alkenyl, or alkynyl chain is optionally substituted with one or more (e.g., 1, 2, 3, 4, 5, or 6) groups independently selected from halogen, $C_{1-4}$ alkyl, $C_{1-4}$ alkoxy, $C_{2-4}$ alkenyl, $C_{2-4}$ alkynyl, $C_{1-4}$ alkoxy, $C_{3-6}$ cycloalkyl, and $C_{3-6}$ cycloalkoxy. In some embodiments, the alkyl, alkenyl, or alkynyl chain can be optionally substituted one or more (e.g., 1, 2, 3, 4, 5, or 6) groups independently selected from halogen, optionally substituted alkyl (e.g., $C_{1-6}$ alkyl), optionally substituted heteroalkyl (e.g., $C_{1-6}$ heteroalkyl, e.g., with 1 or 2 heteroatoms independently selected from oxygen and nitrogen), optionally substituted alkenyl (e.g., $C_{2-6}$ alkenyl), optionally substituted alkynyl (e.g., $C_{2-6}$ alkynyl), optionally substituted cycloalkyl (e.g., $C_{3-6}$ cycloalkyl), optionally substituted aryl (e.g., $C_{6-14}$ aryl), optionally substituted heterocycloalkyl (e.g., 5-8 membered heterocycloalkyl), optionally substituted heteroaryl (e.g., 5-10 membered heteroaryl), short peptides (e.g. mono, di, tri, or tetra-peptides), —$NR^{100}R^{101}$, —$C(=O)NR^{100}R^{101}$, —$COOR^{102}$, and —$OR^{102}$, wherein $R^{100}$, $R^{101}$, and $R^{102}$ are each independently hydrogen, optionally substituted alkyl (e.g., $C_{1-6}$ alkyl), optionally substituted heteroalkyl (e.g., $C_{1-6}$ heteroalkyl, e.g., with 1 or 2 heteroatoms independently selected from oxygen and nitrogen), optionally substituted cycloalkyl (e.g., $C_{3-6}$ cycloalkyl), optionally substituted aryl (e.g., $C_{6-14}$ aryl), optionally substituted heterocycloalkyl (e.g., 5-8 membered heterocycloalkyl), optionally substituted heteroaryl (e.g., 5-10 membered heteroaryl), wherein each of the optionally substituted groups is independently optionally substituted with one or more (e.g., 1-3) substituents selected from oxo, halogen, hydroxyl, $NH_2$, —$NH(C_{1-4}$ alkyl), —$N(C_{1-4}$ alkyl)$(C_{1-4}$ alkyl), $C_{1-4}$ alkyl optionally substituted with 1-3 fluorine, $C_{1-4}$ alkoxy optionally substituted with 1-3 fluorine, $C_{2-4}$ alkenyl, $C_{2-4}$ alkynyl, $C_{3-6}$ cycloalkyl optionally substituted with 1-3 fluorine or 1-2 $C_{1-4}$ alkyl, and $C_{3-6}$ cycloalkoxy optionally substituted with 1-3 fluorine or 1-2 $C_{1-4}$ alkyl. In some embodiments, In some embodiments, the short peptides can be a mono-, di-, tri-, or tetra-peptide, which can be derived from alpha-amino acids (e.g., D or L-amino acids) selected from alanine, isoleucine, leucine, methionine, valine, phenylalanine, tryptophan, tyrosine, asparagine, cysteine, glutamine, serine, threonine, aspartic acid, glutamic acid, arginine, histidine, lysine, glycine, and proline. In some embodiments, $R^1$ is an unsubstituted straight alkyl chain having 7-30 (e.g., 10-24) carbons. In some embodiments, $R^1$ is an unsubstituted branched alkyl chain having 7-30 (e.g., 10-24) carbons. In some embodiments, $R^1$ is an unsubstituted straight alkyl chain having a formula of $CH_3(CH_2)_n$—, wherein n is an integer of 8-24 (e.g., 10-24). In some specific embodiments, $R^1$ is selected from $CH_3(CH_2)_{10}$—, $CH_3(CH_2)_{12}$—, $CH_3(CH_2)_{14}$—, and $CH_3(CH_2)_{16}$—.

In some embodiments, the present disclosure also provides a prodrug of hydromorphone. In some embodiments, the prodrug is a compound of Formula 2, or a pharmaceutically acceptable salt thereof

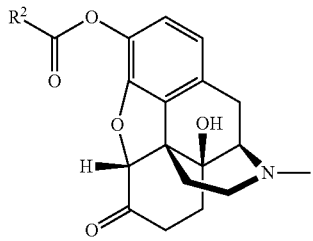

(Formula 2)

wherein $R^2$ is $R^{20}$, —$OR^{20}$, or —$NHR^{20}$, wherein $R^{20}$ is an optionally substituted straight or branched alkyl, alkenyl, or alkynyl chain having a total number of 7-30 carbons. In some embodiments, the alkyl, alkenyl, or alkynyl chain is optionally substituted with one or more hydrophobic groups (e.g., as described herein). In some embodiments, the alkyl, alkenyl, or alkynyl chain is optionally substituted with one or more (e.g., 1, 2, 3, 4, 5, or 6) groups independently selected from halogen, $C_{1-4}$ alkyl, $C_{1-4}$ alkoxy, $C_{2-4}$ alkenyl, $C_{2-4}$ alkynyl, $C_{1-4}$ alkoxy, $C_{3-6}$ cycloalkyl, and $C_{3-6}$ cycloalkoxy. In some embodiments, the alkyl, alkenyl, or alkynyl chain can be optionally substituted one or more (e.g., 1, 2, 3, 4, 5, or 6) groups independently selected from halogen, optionally substituted alkyl (e.g., $C_{1-6}$ alkyl), optionally substituted heteroalkyl (e.g., $C_{1-6}$ heteroalkyl, e.g., with 1 or 2 heteroatoms independently selected from oxygen and nitrogen), optionally substituted alkenyl (e.g., $C_{2-6}$ alkenyl), optionally substituted alkynyl (e.g., $C_{2-6}$ alkynyl), optionally substituted cycloalkyl (e.g., $C_{3-6}$ cycloalkyl), optionally substituted aryl (e.g., $C_{6-14}$ aryl), optionally substituted heterocycloalkyl (e.g., 5-8 membered heterocycloalkyl), optionally substituted heteroaryl (e.g., 5-10 membered heteroaryl), short peptides (e.g. mono, di, tri, or tetra-peptides), —$NR^{100}R^{101}$, —$C(=O)NR^{100}R^{101}$, —$COOR^{102}$, and —$OR^{102}$, wherein $R^{100}$, $R^{101}$, and $R^{102}$ are each independently hydrogen, optionally substituted alkyl (e.g., $C_{1-6}$ alkyl), optionally substituted heteroalkyl (e.g., $C_{1-6}$ heteroalkyl, e.g., with 1 or 2 heteroatoms independently selected from oxygen and nitrogen), optionally substituted cycloalkyl (e.g., $C_{3-6}$ cycloalkyl), optionally substituted aryl (e.g., $C_{6-14}$ aryl), optionally substituted heterocycloalkyl (e.g., 5-8 membered heterocycloalkyl), optionally substituted heteroaryl (e.g., 5-10 membered heteroaryl), wherein each of the optionally substituted groups is independently optionally substituted with one or more (e.g., 1-3) substituents selected from oxo, halogen, hydroxyl, $NH_2$, —$NH(C_{1-4}$ alkyl), —$N(C_{1-4}$ alkyl)$(C_{1-4}$ alkyl), $C_{1-4}$ alkyl optionally substituted with 1-3 fluorine, $C_{1-4}$ alkoxy optionally substituted with 1-3 fluorine, $C_{2-4}$ alkenyl, $C_{2-4}$ alkynyl, $C_{3-6}$ cycloalkyl optionally substituted with 1-3 fluorine or 1-2 $C_{1-4}$ alkyl, and $C_{3-6}$ cycloalkoxy optionally substituted with 1-3 fluorine or 1-2 $C_{1-4}$ alkyl. In some embodiments, In some embodiments, the short peptides can be a mono-, di-, tri-, or tetra-peptide, which can be derived from alpha-amino acids (e.g., D or L-amino acids) selected from alanine, isoleucine, leucine, methionine, valine, phenylalanine, tryptophan, tyrosine, asparagine, cysteine, glutamine, serine, threonine, aspartic acid, glutamic acid, arginine, histidine, lysine, glycine, and proline. In some embodiments, $R^2$ is an unsubstituted straight alkyl chain having 7-30 (e.g., 10-24) carbons. In some embodiments, $R^2$ is an unsubstituted branched alkyl chain having 7-30 (e.g., 10-24) carbons. In some embodiments, $R^2$ is an unsubstituted straight alkyl chain having a formula of $CH_3(CH_2)_n$—, wherein n is an integer of 8-24 (e.g., 10-24). In some specific embodiments, $R^2$ is selected from $CH_3(CH_2)_{10}$—, $CH_3(CH_2)_{12}$—, $CH_3(CH_2)_{14}$—, and $CH_3(CH_2)_{16}$—.

In some embodiments, the present disclosure also provides specific prodrugs which can be any one of Compound Nos. 1-8 (see the Examples section), or a pharmaceutically acceptable salt thereof.

TABLE 1
List of Exemplary Schedule II, III and IV Controlled Substance as defined by the
United States Controlled Substances Act
| ACSCN | Class | Drug | Chemical Structure |
|---|---|---|---|
| 9050 | opiate | Codeine | 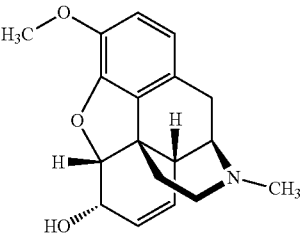 |
| 9334 | opiate | Dihydroetorphine | 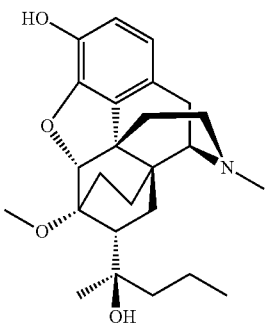 |
| 9190 | opiate | Ethylmorphine | 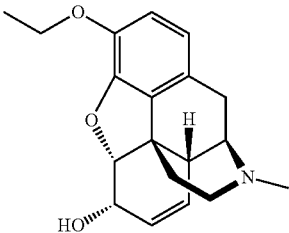 |
| 9059 | opiate | Etorphine | 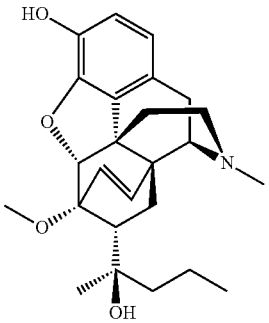 |
| 9150 | opiate | Hydromorphone | 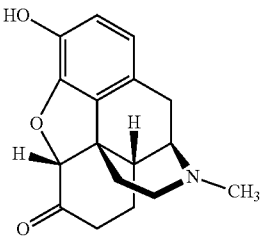 |

TABLE 1-continued
List of Exemplary Schedule II, III and IV Controlled Substance as defined by the United States Controlled Substances Act
| ACSCN | Class | Drug | Chemical Structure |
|---|---|---|---|
| 9260 | opiate | Metopon | 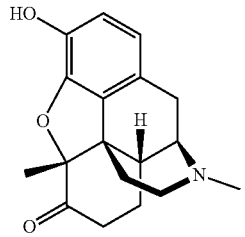 |
| 9300 | opiate | Morphine | 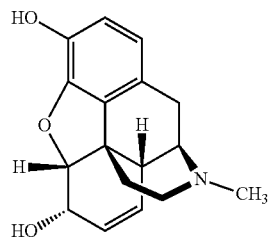 |
| 9330 | opiate | Oripavine | 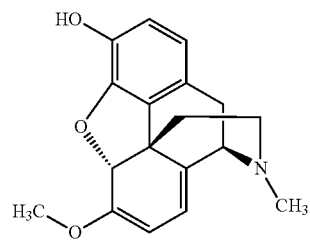 |
| 9143 | opiate | Oxycodone | 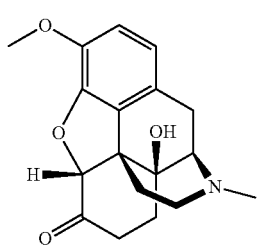 |
| 9652 | opiate | Oxymorphone | 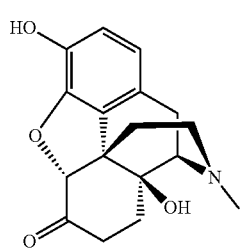 |

TABLE 1-continued
List of Exemplary Schedule II, III and IV Controlled Substance as defined by the United States Controlled Substances Act
| ACSCN | Class | Drug | Chemical Structure |
|---|---|---|---|
| 9020 | opiate | Anileridine | 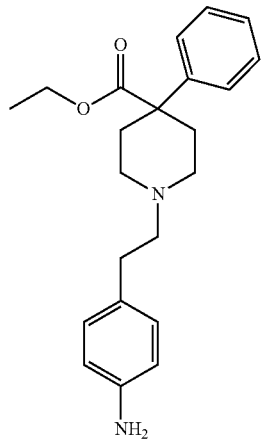 [SMILES: CCOC(=O)C1(c2ccccc2)CCN(CCc2ccc(N)cc2)CC1] |
| 9180 | stimulant | Ecgonine | 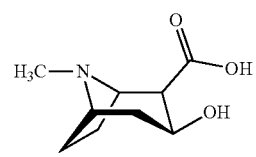 |
| 9120 | opiate | Dihydrocodeine | 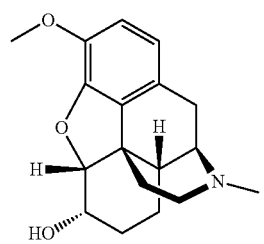 |
| 9220 | opiate | Levorphanol | 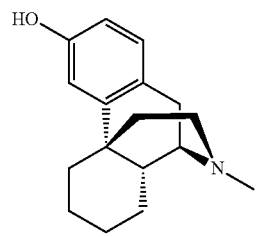 |
| 9240 | opiate | Metazocine | 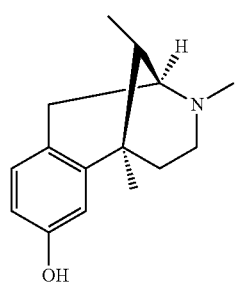 [SMILES: CC1[C@@H]2Cc3ccc(O)cc3[C@@]1(C)CCN2C] |

TABLE 1-continued
List of Exemplary Schedule II, III and IV Controlled Substance as defined by the United States Controlled Substances Act
| ACSCN | Class | Drug | Chemical Structure |
|---|---|---|---|
| 9715 | opiate | Phenazocine | 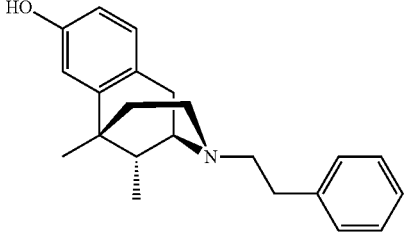 |
| 9730 | opiate | Piminodine | 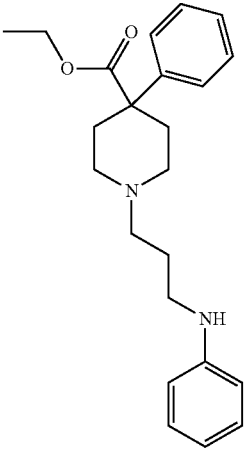 [SMILES: CCOC(=O)C1(c2ccccc2)CCN(CCCNc2ccccc2)CC1] |
| 9733 | opiate | Racemorphan | 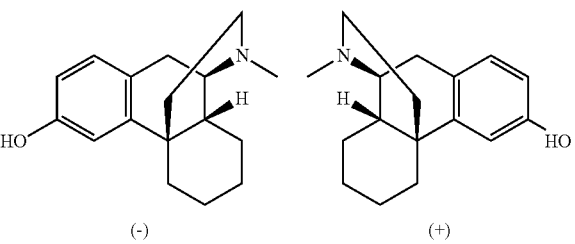 |
| 9780 | opiate | Tapentadol | 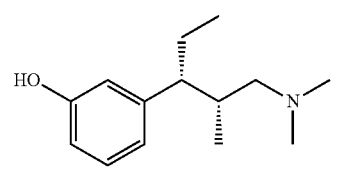 [SMILES: CC[C@@H](c1cccc(O)c1)[C@@H](C)CN(C)C] |
| 1100 | stimulant | Amphetamine | 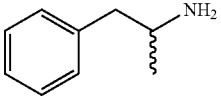 |
| 1105 | stimulant | Methamphetamine | 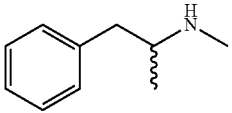 |

TABLE 1-continued
List of Exemplary Schedule II, III and IV Controlled Substance as defined by the United States Controlled Substances Act
| ACSCN | Class | Drug | Chemical Structure |
|---|---|---|---|
| 1631 | stimulant | Phenmetrazine | 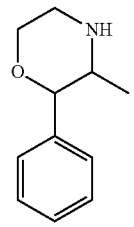 |
| 1724 | stimulant | Methylphenidate | 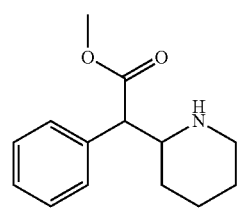 [SMILES: COC(=O)C(c1ccccc1)C1CCCCN1] |
| 1205 | stimulant | Lisdexamfetamine | 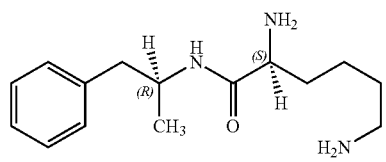 |
| 7379 | hallucinogen | Nabilone | 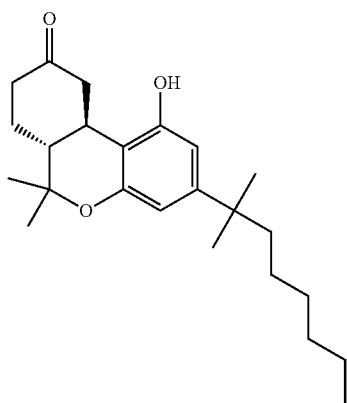 [SMILES: CCCCCCC(C)(C)c1cc(O)c2c(c1)OC(C)(C)[C@@H]1CCC(=O)C[C@@H]21] |
| 1645 | Stimulant | Chlorphentermine | 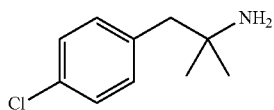 |
| 1647 | Stimulant | Clortermine | 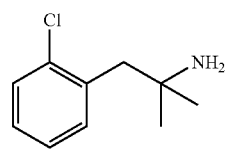 |

TABLE 1-continued

List of Exemplary Schedule II, III and IV Controlled Substance as defined by the United States Controlled Substances Act

| ACSCN | Class | Drug | Chemical Structure |
|---|---|---|---|
| 2126 | Depressant | Amobarbital | 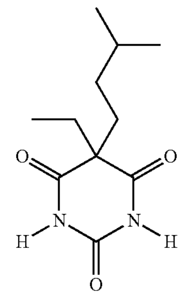 [SMILES: CCC1(CCC(C)C)C(=O)NC(=O)NC1=O] |
| 2510 | Depressant | Chlorhexadol | 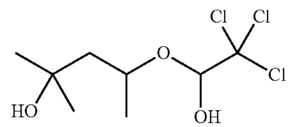 |
| 2020 | Depressant | Embutramide | 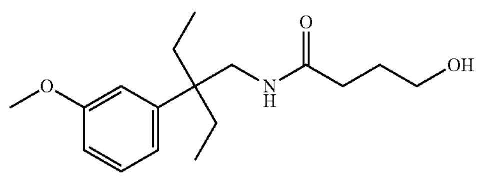 [SMILES: CCC(CC)(CNC(=O)CCCO)c1cccc(OC)c1] |
| 2012 | Depressant | Xyrem | 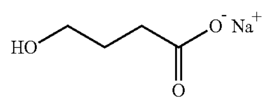 |
| 7285 | Depressant | Ketamine | 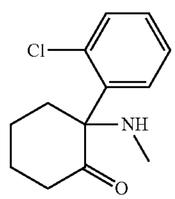 [SMILES: CNC1(c2ccccc2Cl)CCCCC1=O] |
| 2575 | Depressant | Methyprylon | 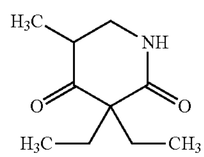 |
| 7295 | Depressant | Tiletamine | 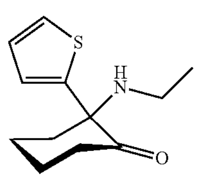 |
| 9400 | opiate | Nalorphine | 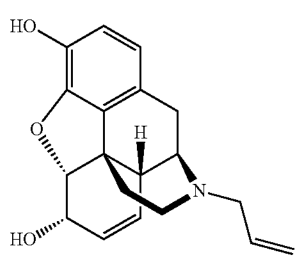 |

TABLE 1-continued

List of Exemplary Schedule II, III and IV Controlled Substance as defined by the
United States Controlled Substances Act

| ACSCN | Class | Drug | Chemical Structure |
|---|---|---|---|
| 9064 | opiate | Buprenorphine | 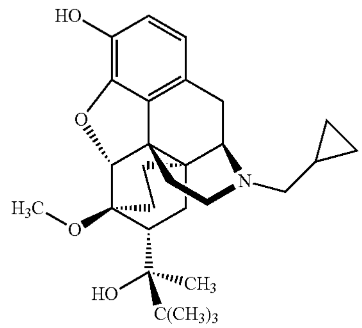 |
| 7300 | Hallucinogen | Lysergic acid | 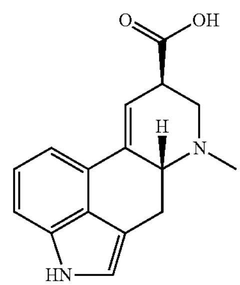 |
| 7310 | Hallucinogen | Lysergic acid | 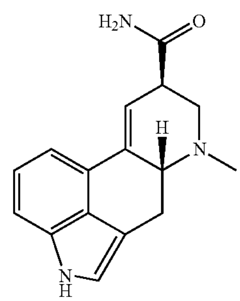 |
| 9752 | Opiate | Tramadol | (1R,2R)-tramadol    (1S,2S)-tramadol |
| 1625 | | Lorcaserin | 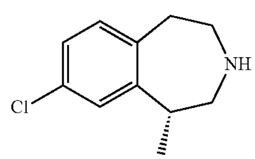 |
| 1230 | Stimulant | Cathine | 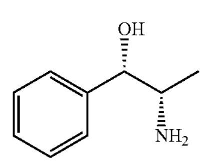 |

TABLE 1-continued

List of Exemplary Schedule II, III and IV Controlled Substance as defined by the United States Controlled Substances Act

| ACSCN | Class | Drug | Chemical Structure |
|---|---|---|---|
| 1760 | Stimulant | Fencamfamin | 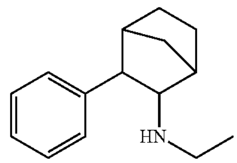 [SMILES: CCNC1C2CCC(C2)C1c1ccccc1] |
| 1575 | Stimulant | Fenproporex | 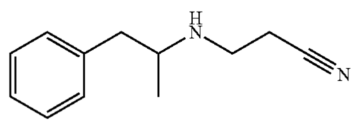 |
| 1605 | Stimulant | Mazindol | 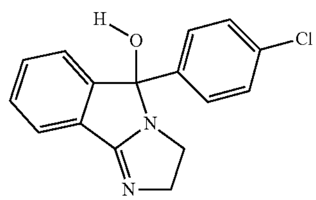 [SMILES: OC1(c2ccc(Cl)cc2)c2ccccc2C2=NCCN21] |
| 1580 | Stimulant | Mefenorex | 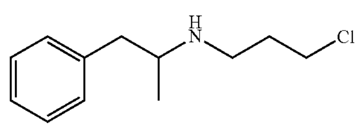 |
| 1680 | Stimulant | Modafinil and stereoisomer armodafinil | 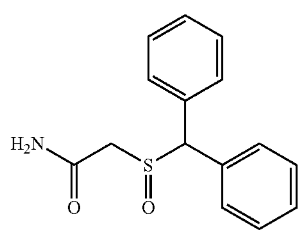 [SMILES: NC(=O)CS(=O)C(c1ccccc1)c1ccccc1] |
| 1530 | Stimulant | Pemoline | 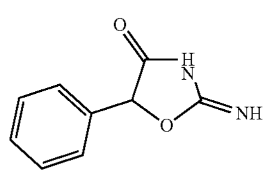 [SMILES: N=C1NC(=O)C(c2ccccc2)O1] |
| 1640 | Stimulant | Phentermine | 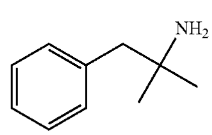 |
| 1750 | Stimulant | Pipradrol | 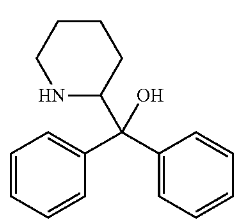 [SMILES: OC(c1ccccc1)(c1ccccc1)C1CCCCN1] |

TABLE 1-continued
List of Exemplary Schedule II, III and IV Controlled Substance as defined by the United States Controlled Substances Act
| ACSCN | Class | Drug | Chemical Structure |
|---|---|---|---|
| 9709 | Opiate | Pentazocine | 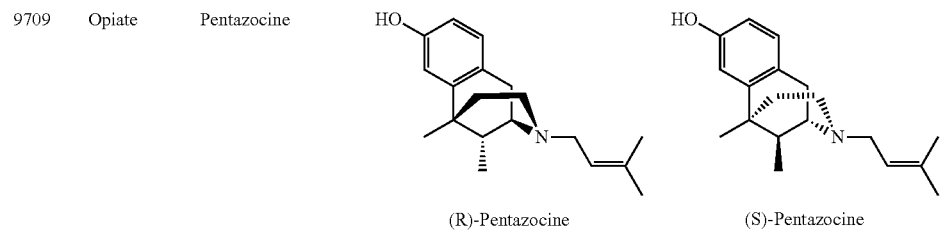<br>(R)-Pentazocine     (S)-Pentazocine |
| 9720 | Opiate | Butorphanol | 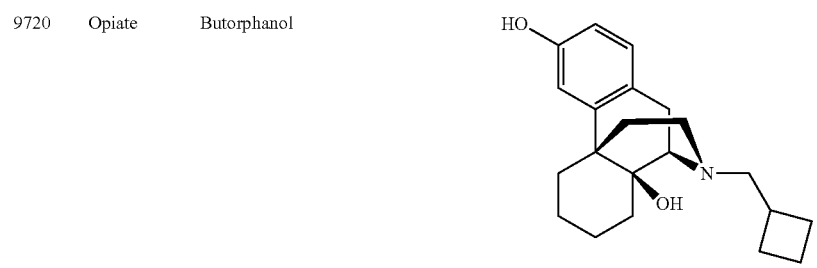 |
| 2145 | Depressant | Barbital | 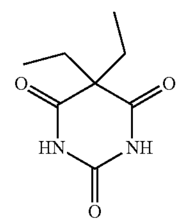 |
| 2748 | Depressant | Bromazepam | 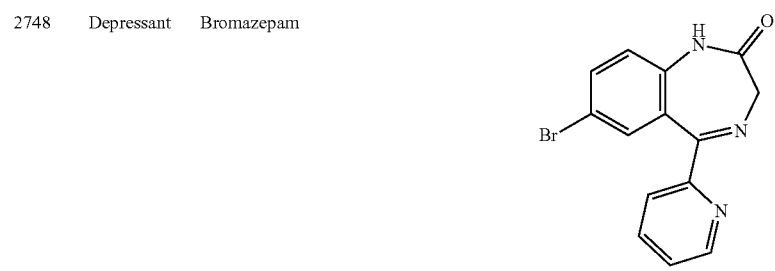 |
| 8192 | Depressant | Carisoprodol | 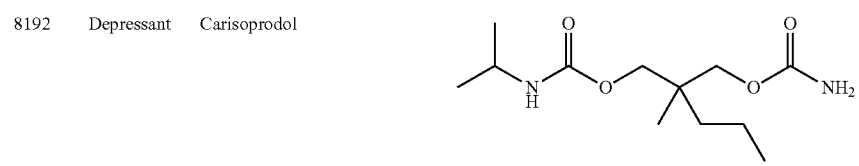 |
| 2465 | Depressant | Chloral hydrate | 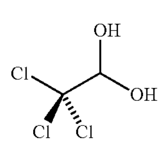 |

TABLE 1-continued

List of Exemplary Schedule II, III and IV Controlled Substance as defined by the
United States Controlled Substances Act

| ACSCN | Class | Drug | Chemical Structure |
|---|---|---|---|
| 2744 | Depressant | Chlordiazepoxide | 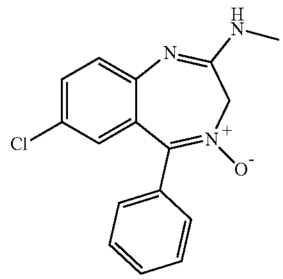 |
| 2737 | Depressant | Clonazepam | 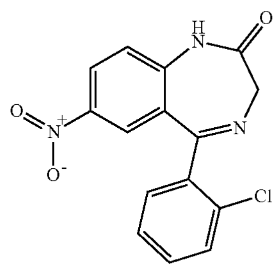 |
| 2768 | Depressant | Clorazepate | 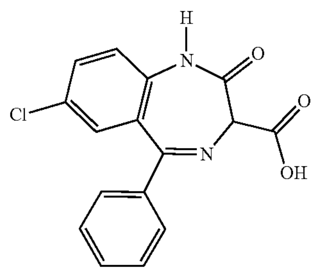 [SMILES: O=C(O)C1N=C(c2ccccc2)c2cc(Cl)ccc2NC1=O] |
| 2753 | Depressant | Cloxazolam | 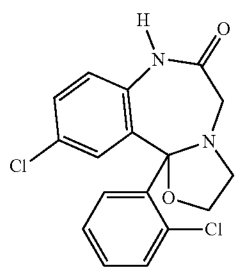 [SMILES: O=C1CN2CCOC2(c2ccccc2Cl)c2cc(Cl)ccc2N1] |
| 2754 | Depressant | Delorazepam | 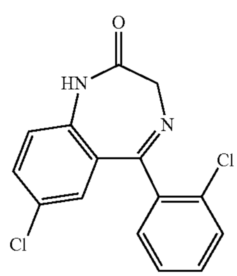 [SMILES: O=C1CN=C(c2ccccc2Cl)c2cc(Cl)ccc2N1] |
| 2540 | Depressant | Ethchlorvynol | 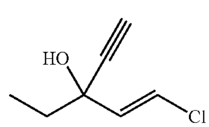 |

TABLE 1-continued

List of Exemplary Schedule II, III and IV Controlled Substance as defined by the
United States Controlled Substances Act

| ACSCN | Class | Drug | Chemical Structure |
|---|---|---|---|
| 2545 | Depressant | Ethinamate | 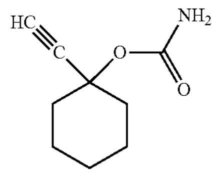 |
| 2758 | Depressant | Ethyl loflazepate | 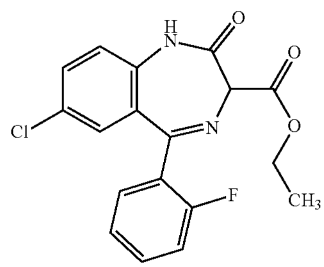 [SMILES: CCOC(=O)C1N=C(c2ccccc2F)c2cc(Cl)ccc2NC1=O] |
| 2771 | Depressant | Haloxazolam | 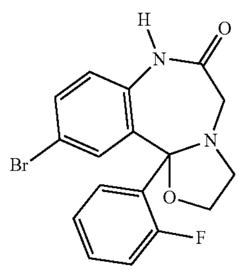 [SMILES: O=C1CN2CCOC2(c2ccccc2F)c2cc(Br)ccc2N1] |
| 2885 | Depressant | Lorazepam | 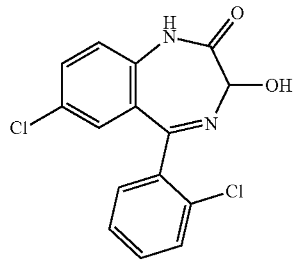 [SMILES: O=C1Nc2ccc(Cl)cc2C(c2ccccc2Cl)=NC1O] |
| 2774 | Depressant | Lormetazepam | 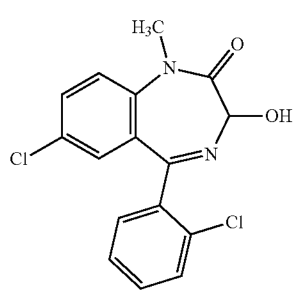 [SMILES: CN1C(=O)C(O)N=C(c2ccccc2Cl)c2cc(Cl)ccc21] |
| 2800 | Depressant | Mebutamate | 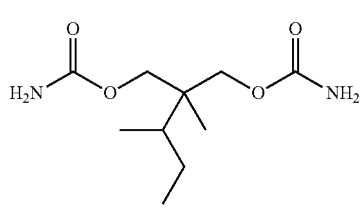 [SMILES: CCC(C)C(C)(COC(N)=O)COC(N)=O] |

TABLE 1-continued
List of Exemplary Schedule II, III and IV Controlled Substance as defined by the United States Controlled Substances Act
| ACSCN | Class | Drug | Chemical Structure |
|---|---|---|---|
| 2820 | Depressant | Meprobamate | 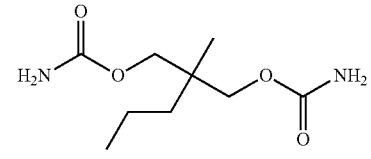 |
| 2264 | Depressant | Methohexital | 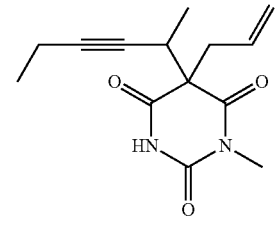 |
| 2250 | Depressant | Methylphenobarbital (mephobarbital) | 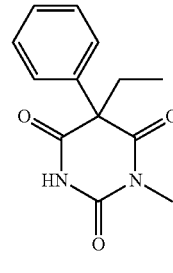 |
| 2834 | Depressant | Nitrazepam | 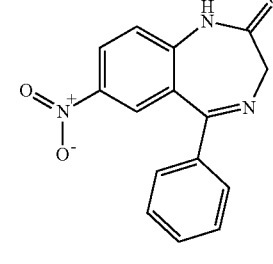 |
| 2838 | Depressant | Nordiazepam | 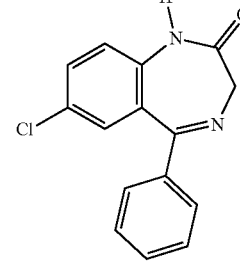 |
| 2835 | Depressant | Oxazepam | 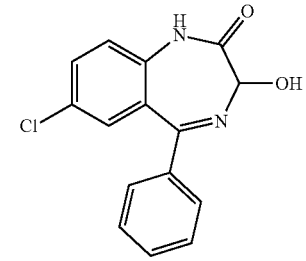 [SMILES: O=C1Nc2ccc(Cl)cc2C(c2ccccc2)=NC1O] |

TABLE 1-continued
List of Exemplary Schedule II, III and IV Controlled Substance as defined by the
United States Controlled Substances Act
| ACSC N | Class | Drug | Chemical Structure |
|---|---|---|---|
| 2839 | Depressant | Oxazolam | 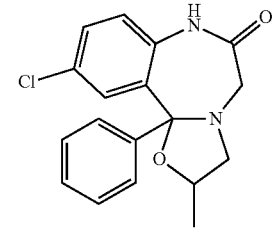 [SMILES: CC1CN2CC(=O)Nc3ccc(Cl)cc3C2(c2ccccc2)O1] |
| 2285 | Depressant | Phenobarbital | 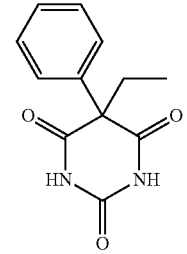 [SMILES: CCC1(c2ccccc2)C(=O)NC(=O)NC1=O] |
| 2886 | Depressant | Temazepam | 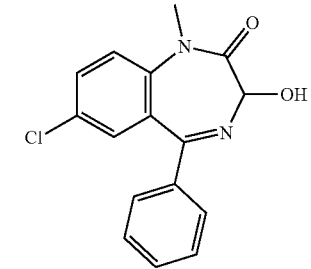 [SMILES: CN1C(=O)C(O)N=C(c2ccccc2)c2cc(Cl)ccc21] |
| 1645 | Stimulant | Chlorphentermine | 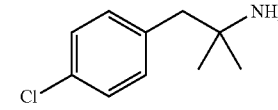 |
| 1647 | Stimulant | Clortermine | 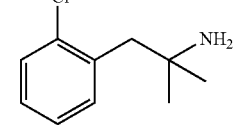 |
| 2126 | Depressant | Amobarbital | 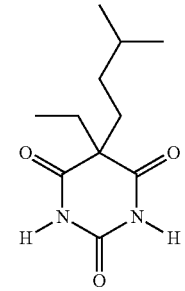 |
| 2510 | Depressant | Chlorhexadol | 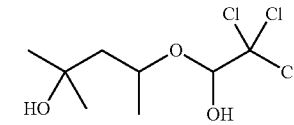 |

TABLE 1-continued

List of Exemplary Schedule II, III and IV Controlled Substance as defined by the United States Controlled Substances Act

| ACSCN | Class | Drug | Chemical Structure |
|---|---|---|---|
| 2020 | Depressant | Embutramide | 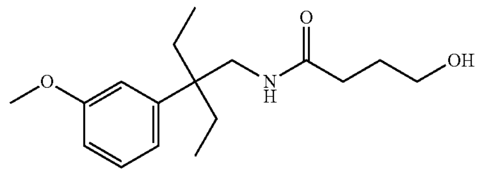 [SMILES: CCC(CC)(CNC(=O)CCCO)c1cccc(OC)c1] |
| 2012 | Depressant | Xyrem | 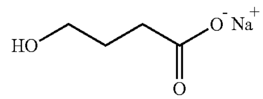 |
| 7285 | Depressant | Ketamine | 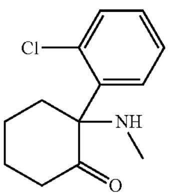 [SMILES: CNC1(c2ccccc2Cl)CCCCC1=O] |
| 2575 | Depressant | Methyprylon | 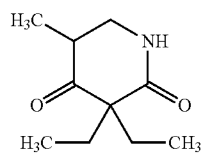 |
| 7295 | Depressant | Tiletamine | 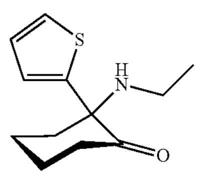 |
| 9400 | opiate | Nalorphine | 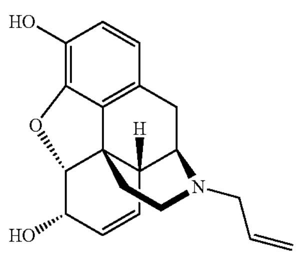 |
| 9064 | opiate | Buprenorphine | 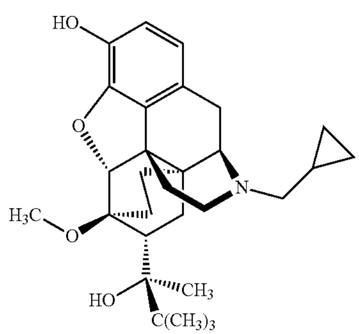 |

TABLE 1-continued

List of Exemplary Schedule II, III and IV Controlled Substance as defined by the
United States Controlled Substances Act

| ACSCN | Class | Drug | Chemical Structure |
|---|---|---|---|
| 7300 | Hallucinogen | Lysergic acid | 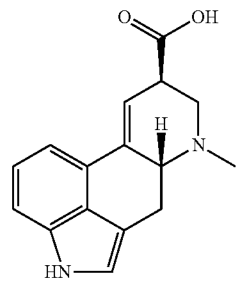 |
| 7310 | Hallucinogen | Lysergic acid amide | 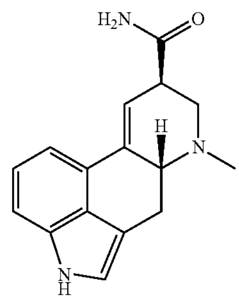 |
| 9752 | Opiate | Tramadol | (1R,2R)-tramadol   (1S,2S)-tramadol |
| 1625 | | Lorcaserin | 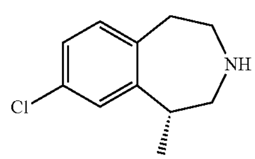 |
| 1230 | Stimulant | Cathine | 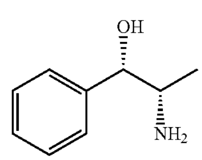 |
| 1760 | Stimulant | Fencamfamin | 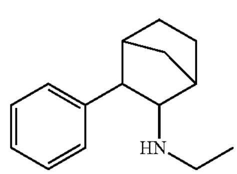 [SMILES: CCNC1C2CCC(C2)C1c1ccccc1] |
| 1575 | Stimulant | Fenproporex | 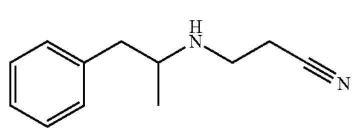 |

TABLE 1-continued

List of Exemplary Schedule II, III and IV Controlled Substance as defined by the United States Controlled Substances Act

| ACSCN | Class | Drug | Chemical Structure |
|---|---|---|---|
| 1605 | Stimulant | Mazindol | 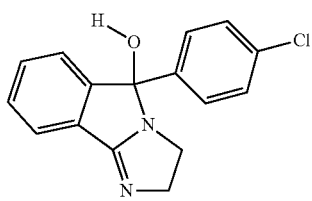 [SMILES: OC1(c2ccc(Cl)cc2)c2ccccc2C2=NCCN21] |
| 1580 | Stimulant | Mefenorex | 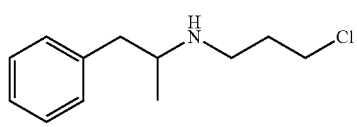 |
| 1680 | Stimulant | Modafinil and stereoisomer armodafinil | 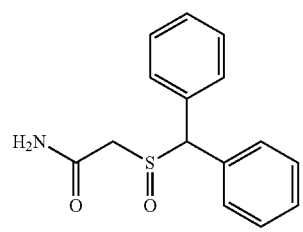 [SMILES: NC(=O)CS(=O)C(c1ccccc1)c1ccccc1] |
| 1530 | Stimulant | Pemoline | 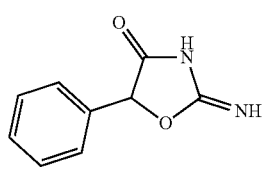 [SMILES: N=C1NC(=O)C(c2ccccc2)O1] |
| 1640 | Stimulant | Phentermine | 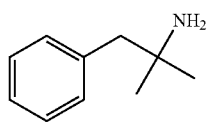 |
| 1750 | Stimulant | Pipradrol | 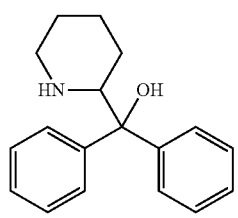 [SMILES: OC(c1ccccc1)(c1ccccc1)C1CCCCN1] |
| 9709 | Opiate | Pentazocine | 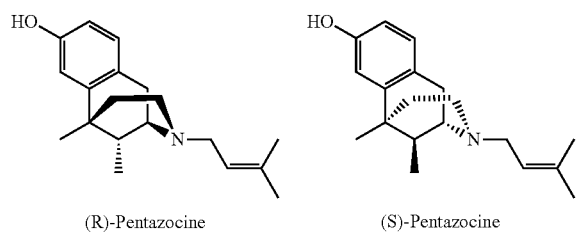 |

(R)-Pentazocine    (S)-Pentazocine

TABLE 1-continued
List of Exemplary Schedule II, III and IV Controlled Substance as defined by the United States Controlled Substances Act
| ACSCN | Class | Drug | Chemical Structure |
|---|---|---|---|
| 9720 | Opiate | Butorphanol | 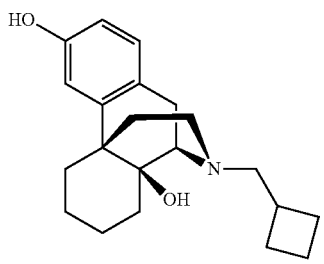 |
| 2145 | Depressant | Barbital | 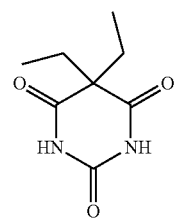 |
| 2748 | Depressant | Bromazepam | 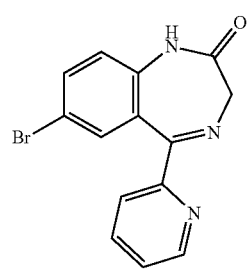 [SMILES: O=C1CN=C(c2ccccn2)c2cc(Br)ccc2N1] |
| 8192 | Depressant | Carisoprodol | 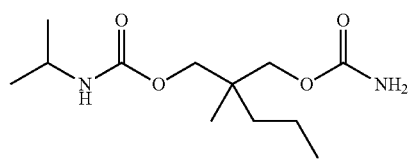 [SMILES: CCCC(C)(COC(N)=O)COC(=O)NC(C)C] |
| 2465 | Depressant | Chloral hydrate | 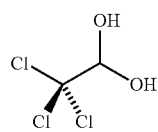 |
| 2744 | Depressant | Chlordiazepoxide | 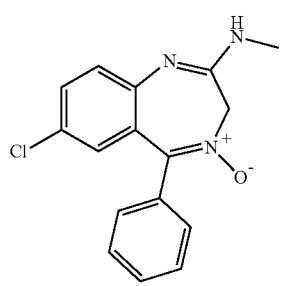 |

TABLE 1-continued
List of Exemplary Schedule II, III and IV Controlled Substance as defined by the United States Controlled Substances Act
| ACSC N | Class | Drug | Chemical Structure |
|---|---|---|---|
| 2737 | Depressant | Clonazepam | 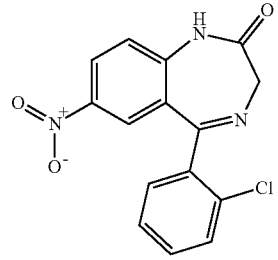 |
| 2768 | Depressant | Clorazepate | 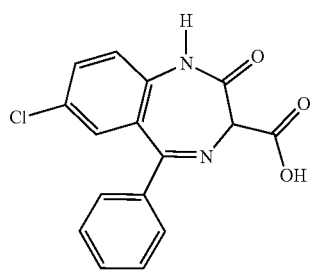 [SMILES: O=C(O)C1N=C(c2ccccc2)c2cc(Cl)ccc2NC1=O] |
| 2753 | Depressant | Cloxazolam | 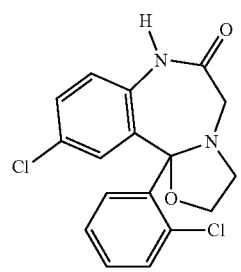 [SMILES: O=C1CN2CCOC2(c2ccccc2Cl)c2cc(Cl)ccc2N1] |
| 2754 | Depressant | Delorazepam | 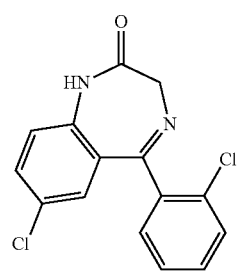 [SMILES: O=C1CN=C(c2ccccc2Cl)c2cc(Cl)ccc2N1] |
| 2540 | Depressant | Ethchlorvynol | 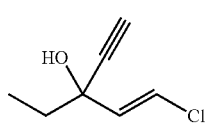 |
| 2545 | Depressant | Ethinamate | 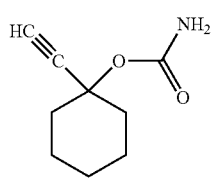 |

TABLE 1-continued
List of Exemplary Schedule II, III and IV Controlled Substance as defined by the
United States Controlled Substances Act
| ACSCN | Class | Drug | Chemical Structure |
|---|---|---|---|
| 2758 | Depressant | Ethyl loflazepate | 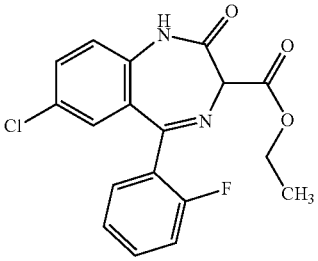 |
| 2771 | Depressant | Haloxazolam | 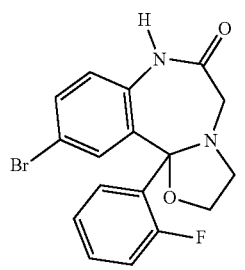 |
| 2885 | Depressant | Lorazepam | 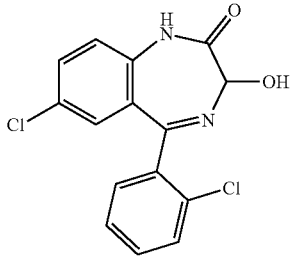 [SMILES: O=C1Nc2ccc(Cl)cc2C(c2ccccc2Cl)=NC1O] |
| 2774 | Depressant | Lormetazepam | 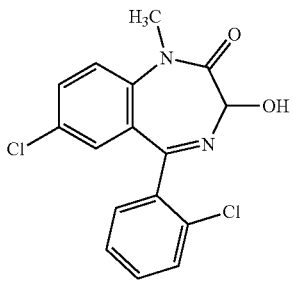 [SMILES: CN1C(=O)C(O)N=C(c2ccccc2Cl)c2cc(Cl)ccc21] |
| 2800 | Depressant | Mebutamate | 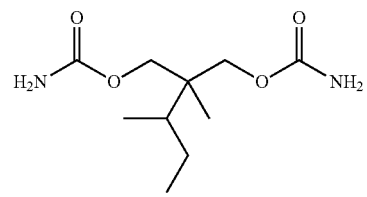 [SMILES: CCC(C)C(C)(COC(N)=O)COC(N)=O] |
| 2820 | Depressant | Meprobamate | 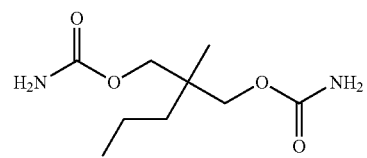 |

TABLE 1-continued

List of Exemplary Schedule II, III and IV Controlled Substance as defined by the
United States Controlled Substances Act

| ACSCN | Class | Drug | Chemical Structure |
|---|---|---|---|
| 2264 | Depressant | Methohexital | 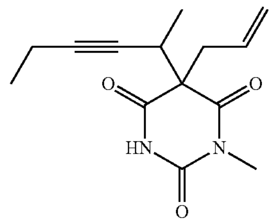 [SMILES: C=CCC1(C(C)C#CCC)C(=O)NC(=O)N(C)C1=O] |
| 2250 | Depressant | Methylphenobarbital (mephobarbital) | 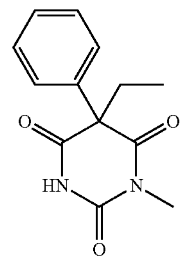 [SMILES: CCC1(c2ccccc2)C(=O)NC(=O)N(C)C1=O] |
| 2834 | Depressant | Nitrazepam | 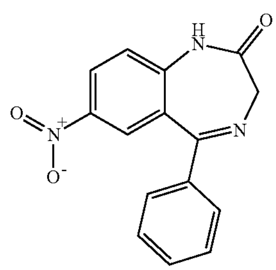 |
| 2838 | Depressant | Nordiazepam | 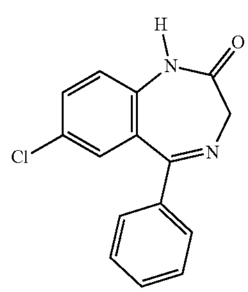 [SMILES: O=C1CN=C(c2ccccc2)c2cc(Cl)ccc2N1] |
| 2835 | Depressant | Oxazepam | 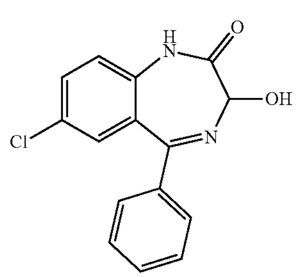 [SMILES: O=C1Nc2ccc(Cl)cc2C(c2ccccc2)=NC1O] |

TABLE 1-continued

List of Exemplary Schedule II, III and IV Controlled Substance as defined by the
United States Controlled Substances Act

| ACSCN | Class | Drug | Chemical Structure |
|---|---|---|---|
| 2839 | Depressant | Oxazolam | 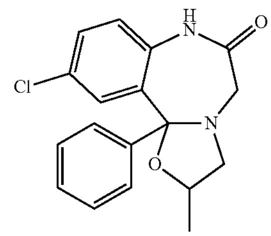 [SMILES: CC1CN2CC(=O)Nc3ccc(Cl)cc3C2(c2ccccc2)O1] |
| 1185 | Depressant | Phenobarbital | 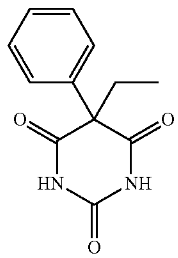 [SMILES: CCC1(c2ccccc2)C(=O)NC(=O)NC1=O] |
| 2886 | Depressant | Temazepam | 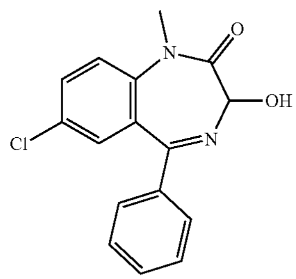 [SMILES: CN1C(=O)C(O)N=C(c2ccccc2)c2cc(Cl)ccc21] |

It is understood that some compounds described herein can exist as stereoisomeric forms including e.g., R-, S- and racemic (RS-) forms. Where the compound has more than one chiral centers, all diastereomers are contemplated herein. When the stereochemistry of a chiral center in a compound is specifically designated, in a drawing or otherwise, it should be understood that the compound exists mainly in the designated stereoisomeric form with regard to the chiral center, for example, with less than 20%, less than 15%, less than 10%, less than 5%, less than 1%, or non-detectable level of the other stereoisomer. Unless expressly indicated otherwise, all stereoisomer forms are contemplated herein.

The prodrugs of the present disclosure can be generally prepared by coupling the corresponding controlled substance with the lipid, substituted lipid, biodegradable natural or synthetic polymers under suitable conditions. In some embodiments, a carbonyl donor agent, phosphoryl donor agent, etc. can also be used to link the controlled substance with the lipid, biodegradable natural or synthetic polymers. Various coupling methods can be used for the preparation of the prodrugs herein, which include those known in the art and also are exemplified in the Examples section.

For example, synthesis of the long-chain fatty acid ester prodrugs of oxymorphone and hydromorphone can be carried out using an approach shown in Example 1 and Example 2 respectively, wherein the long-chain fatty acid is converted into an activated form, such as the corresponding acyl chloride using an activating agent such as $SOCl_2$. The resulting activated form, such as acyl chloride, can then be coupled to the phenolic hydroxyl group of hydromorphone and oxymorphone to give the long-chain fatty acid ester opioid prodrug. In view of the present disclosure, the prodrugs of the present disclosure can be readily prepared by those skilled in the art.

In another aspect, the present disclosure also provides processes and novel intermediates disclosed herein which are useful for preparing the prodrugs of the present disclosure. In other aspects, methods for synthesis, analysis, separation, isolation, purification, characterization, and testing of the prodrugs of the present disclosure are provided.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", 4th ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wis., USA), Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7$^{th}$ Edition), and Larock's Comprehensive Organic Transformations (Wiley-VCH, 1999).

III. Methods of Use

The prodrugs of the present disclosure are useful for the treatment of any of the diseases or disorders where administering the parent drugs (controlled substances) are useful. For example, in some embodiments, the controlled substance is an analgesic, and the prodrugs of such controlled substance can be used in a method for treating pain (e.g., chronic pain).

Accordingly, in some embodiments, the present disclosure provides a method of treating pain (e.g., chronic pain), the method comprising administering to a subject in need thereof pain treatment a therapeutically effective amount of a prodrug of the present disclosure (e.g., Formula I, I-X, 1 or 2) or a pharmaceutical composition comprising the prodrug, wherein the prodrug is a prodrug of an analgesic (e.g., an opioid such as a phenolic opioid). In some embodiments, the prodrug is a compound of Formula I-X, or a pharmaceutically acceptable salt thereof, wherein D is a residue of a controlled substance listed in Table 1 that is an analgesic, e.g., any of the opioid or phenolic opioid listed in Table 1. In some embodiments, D is a residue of morphine, oxymorphone, hydromorphone, levorphanol, or oxycodone. In some embodiments, the prodrug is a compound of Formula 1 or 2, or a pharmaceutically acceptable salt thereof. In some embodiments, the prodrug is any one of Compound Nos. 1-8, or a pharmaceutically acceptable salt thereof. In some embodiments, the administering can be an injection, such as a subcutaneous or intramuscular injection. As shown in the Examples section, intramuscular injection of a few exemplary prodrugs of the present disclosure was shown to slowly release the corresponding parent drug (e.g., oxymorphone or hydromorphone) in vivo and thus can provide a long-lasting effect. This release profile can be advantageous at least in that it allows a less frequent administration and better patient compliance. Also, as the prodrug is administered via injection, the formulation can be restricted to hospital use, which therefore can greatly reduce the likelihood of an abuser obtaining a large quantity of the prodrug for attempted extractions (or otherwise attempted tampering) of the controlled substance. Further, as the controlled substance or a metabolite thereof is only released slowly after administration, the abuser's potential reward of euphoria may not be achieved by simply injecting the formulation. As such, the potential for abuse is also reduced.

In some embodiments, the prodrugs of the present disclosure can be used for preparing an abuse deterrent formulation. As described herein, the inventors also designed the prodrugs and pharmaceutical compositions comprising the same to effectively resist some or all chemical and physical conditions that are commonly used by drug abusers, including chewing, crushing, injection, and inhalation, or simple extraction with organic solvents. The term "abuse deterrent" and "abuse resistant" are used herein interchangeably, both of which do not require full prevention of abuse. Abuse deterrent or resistant properties/methods include, but are not limited to, any of the properties/methods described herein as useful for deterring drug abuse, such as properties that allow a formulation to be resistant to common hydrolysis conditions by potential abusers, methods of restricting potential abusers' access to the controlled substance, etc. The term "abuse" should be understood as the intentional, non-therapeutic use of a drug product or substance, even once, to achieve a desirable psychological or physiological effect.

In some embodiments, the present disclosure also provide methods of reducing a likelihood of abuse of a controlled substance. In some embodiments, the method comprises providing a prodrug of the controlled substance, wherein the prodrug is a compound of Formula I-X (as defined herein) or a pharmaceutically acceptable salt thereof, wherein D in Formula I-X is a residue of the controlled substance, and formulating the prodrug in an abuse-deterrent formulation. In some embodiments, the prodrug is a compound of Formula I, I-X, 1 or 2, or a pharmaceutically acceptable salt thereof. In some embodiments, the prodrug is a compound of Formula I-X, or a pharmaceutically acceptable salt thereof, wherein D is a residue of a controlled substance listed in Table 1, e.g., any of the opioid or phenolic opioid listed in Table 1. In some embodiments, D is a residue of morphine, oxymorphone, hydromorphone, levorphanol, or oxycodone. In some embodiments, the prodrug can be a compound of Formula 1 or 2 (e.g., any of the Compound Nos. 1-8), or a pharmaceutically acceptable salt thereof. In some embodiments, the abuse-deterrent formulation is an injectable formulation, such as a subcutaneous or intramuscular injectable formulation. In some embodiments, the abuse-deterrent formulation is resistant towards (e.g., substantially stable under) common tampering conditions, such as baking soda or vinegar mediated hydrolysis at pH of about 8.3 or 2.4, respectively, or citric acid mediated hydrolysis at a pH of about 1.6. As used herein, "substantially stable" should be understood as less than 30%, less than 20%, or less than 5% degradation under a given condition, e.g., hydrolysis under common tampering conditions described herein. Thus, even if an abuser can obtain the prodrug formulation, because of the difficulty in obtaining the controlled substance from the prodrug formulation, the likelihood of drug abuse is also reduced. In some embodiments, the abuse-deterrent formulation comprises micelles comprising the prodrug. Without wishing to be bound by theories, it is believed that micelle formation can further reduce the rate of hydrolysis and thus improve the formulation's stability towards common tampering conditions that attempt to recover the controlled substance from the prodrug formulation. In some embodiments, the method further comprising restricting the administration of the abuse-deterrent formulation to a hospital setting. Thus, the method limits access of the prodrug formulation to a potential abuser, which also reduces the likelihood of abuse. In some embodiments, the abuse-deterrent formulation also provides a long acting release of the controlled substance. For example, the abuse-deterrent formulation can, after administration, release the controlled substance, or a metabolite thereof, in a subject user over an extended period of time, such as at least 3 days. As the controlled substance or a metabolite thereof is only released slowly after administration, the abuser's potential reward of euphoria may not be achieved by simply injecting the formulation. As such, the likelihood of abuse is also reduced.

Without wishing to be bound by theories, the following rationales regarding exemplary prodrugs based on long-chain fatty acids further show advantages of the prodrugs and/or methods of the present disclosure, such as the potential to reduce drug abuse by using the prodrugs of the present disclosure or pharmaceutical composition comprising the prodrugs.

Without wishing to be bound by theories, it is believed that the prodrugs based on long-chain fatty acids are stable in physical and chemical conditions to resist tampering. Ester prodrug is usually stable under normal storage conditions. Numerous carboxyl ester prodrugs have been designed to improve the drug permeability and enhance the bioavailability (Williams F M, *Clin Pharmacokinet.* 10(5): 392-403 (1985); Beaumont K et al. *Curr Drug Metab.* 4(6):461-85 (2003)). In order to secure FDA approval, these marketed carboxyl ester prodrugs have to have adequate stability under normal storage conditions, usually, 18-24 months shelf life at room temperature. Carboxyl ester prodrug is also stable under common kitchen chemistry tampering conditions. It has been reported that the pH-stability profile of ester bond is a bell-shaped curve, i.e., ester bond is most stable at pH 3-6 and less stable at more acidic or basic pHs (Mabey W. J. *Phys. Chem. Ref. Data* 7:383 (1978)). The weak acidic and basic conditions generated by kitchen chemicals, such as acetic acid (pH=2.4 at 1.0M), citric acid (pH=1.57 at 1.0M) and baking soda (pH=8.3 at 1.0M), cannot hydrolyze carboxyl ester in hours even at elevated temperature.

Long-chain fatty acid ester provides extra stability under common tampering conditions. The long fatty acid chain greatly decreases the aqueous solubility of the prodrug, which makes it hard to extract or manipulate in aqueous media. For example, the solubility of monomeric laurate was greater than 500 µM, whereas the solubility of monomeric myristate was 20-30 µM. Palmitate, stearate, and oleate solutions, on the other hand, showed a tendency to aggregation even at concentrations below 1 µM (Vorum H et al. *Biochim Biophys Acta.* 22; 1126(2):135-42 (1992)). When solubilized, the long-chain fatty acid ester forms micelles and slows down the acid- or base-catalyzed hydrolysis in aqueous media. Therefore, long-chain fatty acid ester prodrug provides superior tampering resistant properties.

Without wishing to be bound by theories, it is also believed that the enzyme mediated release of the controlled substance from prodrugs based on long-chain fatty acids can be adjusted. Controllable hydrolysis rate can prevent an ester prodrug from releasing the active parent drug immediately following administration into human body. Esterases lack substrate specificity in general. It is widely believed that ester prodrugs are hydrolyzed by various esterases in all tissues. However, it has been reported recently that one carboxylesterase usually predominates with each substrate and serves as the major pathway of hydrolysis. Drugs undergoing hydrolysis by carboxyl ester might be subject to clinically significant alterations in their disposition (Laizure S C et al. *PHARMACOTHERAPY*, 33:210-22 (2013)).

According to Enzyme Commission (EC) of the International Union of Biochemistry (Moss G P, 2011), two categories of enzymes catalyze the hydrolysis of carboxyl ester: carboxylesterases and lipase. The classification is summarized below:

EC 3: hydrolase
EC 3.1: ester hydrolase
EC 3.1.1: carboxyl ester hydrolase
EC 3.1.1.1: carboxylesterases
EC 3.1.1.3: lipases (also called triacylglycerol hydrolases)

There are significant differences between carboxylases and lipases.

(1) Expression Profile: in humans, two carboxylesterases, hCE1 and hCE2, are important mediators of drug metabolism. Both are expressed in the liver, but hCE1 greatly exceeds hCE2. In the intestine, only hCE2 is present and highly expressed (Imai T et al. *Drug Metab Dispos* 34:1734-41 (2006); Zhang W et al. *Appl Immunohistochem Mol Morphol* 10:374 (2002)). Carboxyl ester lipase is primarily expressed in the pancreas and lactating mammary gland, as well as liver, macrophages, and in the vessel wall (Hui D, et al. *Journal of Lipid Research* 43:2017-30 (2002)); (2) Substrate Selectivity: hCE1 catalyzes substrate with small alcohol group and large acyl group, while hCE2 catalyzes substrate with large alcohol group and small acyl group (Imai T., et al. *Drug Metab Dispos* 34:1734-41 (2006)). Lipase primarily hydrolyzes the long-chain fatty acid from triacylglycerol.

(3) Substrate Property: carboxylases catalyze the hydrolysis of short-chain fatty acid ester in solution; Lipases are active on solutions of esters and triacylglycerols, but, in contrast to carboxyl esterases, they all display maximal activity against emulsified substrates.

Desirable enzyme conversion rate can be achieved by selecting an appropriate prodrug as described herein. Firstly, the enzyme catalyzed hydrolysis rate of long-chain fatty acid ester is slower than that of short-chain fatty acid ester. By selecting a longer fatty acid chain, the hydrolysis rate of the ester prodrug can be slowed. Buchwald et al reported that fastest hydrolysis rates is achieved with fatty acid chains that are neither too short nor too long and are of around four carbon-atom long in human blood. (Buchwald P et al. *Pharmazie.* 57(2):87-93 (2002)). In a study of the hydrolysis of fatty acid esters of acetaminophen in buffered pancreatic lipase, Bauguess et al reported that there was a negative relationship between the chain length of the acyl moiety and the corresponding hydrolysis rates. The longer chain esters, p-acetamidophenyl palmitate and p-acetamidophenyl stearate, were hydrolyzed much slower than p-acetamidophenyl decanoate, p-acetamidophenyl laurate, and p-acetamidophenyl myristateunder the same in vitro conditions (Bauguess C T et al. *J Pharm Sci.* 64(1):117-120(1975)). Therefore, an 'extended' release profile can be achieved with appropriate fatty acid chain length.

Secondly, by exploiting the difference between esterases and lipase, prodrugs based on long-chain fatty acid can be used to limit the site of enzyme conversion. Unlike most marketed short-chain fatty acid ester prodrugs, which can be hydrolyzed by either carboxylesterase or other esterases, long-chain fatty acid ester is primarily hydrolyzed by carboxyl ester lipase (CEL) (Lindstrom et al. *Biochim Biophys Acta.* 959(2):178-84 (1988)). The main human CELs are secreted by the pancreas into the digestive system and are involved in the digestion and absorption of lipid. Other human lipases are expressed in vessel walls and may be a protective mechanism against atherosclerosis by reducing lysoPC level in the vasculature. These CELs may also participate in lipoprotein metabolism and atherosclerosis (Li et al. *Biochem. J.* 329:675-679 (1998)). Since the major function of carboxyl ester lipase is digesting food fat and lipid, the expression level of CELs in plasma and blood vessel is much lower than in digestive track (Hui et al. 2002). Therefore, the conversion rate of long-chain fatty acid ester opioid prodrug in plasma is much slower than in digestive tract. The prodrug can also form micelle that remains inactive for carboxyl esterases in plasma. The micelle is gradually taken up and cleaved by lipase in endothelial cell wall and liver, which is also a process too slow to generate the euphoria desired by drug abusers.

Therefore, when inhaled or snorted, long-chain fatty acid ester opioid prodrugs exhibit an 'extended' release profile in the systemic circulation.

Further, as shown in the Examples section, the inventors have confirmed that several exemplary fatty acid based prodrugs of the present disclosure can be formulated in an injectable formulation (e.g., intramuscular injection), which provided a long-lasting release of the controlled substance (e.g., oxymorphone or hydromorphone) over an extended period of time in a rat PK study. It was further observed that by changing the fatty acid chain length, different PK profiles can be observed. Thus, different fatty acid ester prodrugs herein can be used for different applications. Specifically, as shown in Example 6, intramuscular administration of Compound 2 (which has a fatty acid chain length of 16, n=14) in rats provides essentially no exposure of the prodrug in circulation, with a mean ratio of $C_{max}$ of the controlled substance (oxymorphone in the Example) to the prodrug being greater than 20 (21 and 63.7 as shown in Table 2B for two different doses), and a mean ratio of AUC (at the last measurement point in the Example) greater than 150 (151 and 161 as shown in Table 2B for two different doses). In contrast, when the fatty acid chain length was 20 (n=18), different PK profiles were observed. As shown also in Example 6, in the case of the oxymorphone prodrug, intramuscular administration of Compound 3 in rats provides a mean ratio of $C_{max}$ of the controlled substance (oxymorphone in the Example) to the prodrug of around 3 (3.22 as shown in Table 3B for the dose tested), and a mean ratio of AUC (at the last measurement point in the Example) of less than 5 (4.44 as shown in Table 3B for the dose tested). Similarly, in the case of the hydromorphone prodrug, intramuscular administration of Compound 7 in rats provides a mean ratio of $C_{max}$ of the controlled substance (hydromorphone in the Example) to the prodrug of less than 1 (0.757 as shown in Table 4B for the dose tested), and a mean ratio of AUC (at the last measurement point in the Example) of less than 2 (1.56 as shown in Table 4B for the dose tested).

Also without wishing to be bound by theories, it is believed that the prodrugs of the present disclosure can be adjusted to achieve a reduced CNS and inhalation penetration. The primary concern of ester prodrug of opioid is enhanced CNS penetration, which exacerbates the abuse problem. Heroin is a classic example: when the hydroxyl group of morphine molecule is modified by acyl group, the resulting compound, heroin, shows significant CNS penetration due to its improved membrane permeability. As widely accepted, the relationship between the log P value of the compound and its CNS distribution is a bell-curve. It has been reported that the optimal log P value for CNS penetration is 2.8 (Wager et al. *ACS Chem. Neurosci.* 1:420-434 (2010)). Acylation of morphine molecule increased its log P value from 0.89 to 1.58, thus increases its CNS permeability. However, the log P value of the long-chain fatty acid ester is on the high extreme side of the graph (i.e., log P>6), which does not penetrate into the CNS. For the same reason, the long-chain fatty acid ester have minimal penetration through the lung cell membrane when smoked or snorted.

Further, as discussed herein, it is believed that the prodrugs of the present disclosure can be formulated to provide a long-acting release of the controlled substance, which can reduce the likelihood of drug abuse and increase patient compliance. For example, the rat PK data in the Examples section show that injection (e.g., intramuscular injection) of long-chain fatty acid ester prodrugs (e.g., oxymorphone or hydromorphone palmitate or arachidate) can provide the controlled substance over a long period of time, with a respective $T_{1/2}$ of oxymorphone or hydromorphone being more than 100 hours (see e.g., Tables 2B, 3B, and 4B). Without wising to be bound by theories, it is believed that for moderately water-soluble compounds, the addition of long-chain fatty acid significantly decreases the solubility of prodrug. When the resulting lipophilic prodrug is injected via intramuscular route, the prodrug can form a depot at the injection site, slowly converts back to parent drug, and gradually releases into systemic circulation.

Also without wishing to be bound by theories, it is hypothesized that lipidized compounds can achieve long-acting effects by binding to albumin or serum lipoprotein. Albumin is a carrier for fatty acids in plasma (Van der Vusse *Drug Metab. Pharmacokinet* 24:300-307 (2009)). It has 6 to 7 fatty acid binding sites for long-chain fatty acids with affinities in the nanomolar dissociation constant range (Bhattacharya et al. *J. Mol. Biol.* 303:721-732 (2000); Spector et al *J. Lipid Res.* 16:165-179 (1975)). Binding to protein stabilizes the compound and increase its circulation half-life.

Thus, the Examples herein show that the prodrugs of the present disclosure can be used to release the underlying controlled substance slowly. And when the prodrug is administered every 3-4 weeks by injection, such as intramuscular injection, which can be typically restricted to hospital use, the chances of drug abuse and diversion of the controlled substance can be reduced. In addition, the consistent around-the-clock level of the controlled substance, e.g., oxymorphone or hydromorphone, in the plasma, e.g., for the treatment of chronic pain, and a decreased injection frequency can also greatly improve patient adherence and compliance. As discussed herein, the chemistry to make the prodrug is cost-effective and straightforward. And the myriad of potential fatty acids allows tailoring of prodrugs for specific properties.

As would be understood by those skilled in the art, although the Examples section describes examples of two opioids, the teachings of this disclosure have wider applications, and the prodrugs of the present disclosure can be used for developing abuse-resistant products other than the exemplified opioids. For example, all opioids with a free hydroxyl group or keto-tautomers can be modified by this prodrug technology herein. The invention is also applicable to any non-opioid drugs with abuse potential, such as opium derivatives, hallucinogeneic or psychedelic substances, and stimulants as provided in Table 1.

IV. Pharmaceutical Compositions

In another aspect, the present invention provides pharmaceutical compositions comprising any of the prodrugs of the present disclosure (e.g., compounds of Formula I, I-X, 1, or 2, or any one of Compound Nos. 1-8, or pharmaceutically acceptable salt thereof). Typically, the pharmaceutical composition includes a pharmaceutically acceptable excipient and a prodrug of the present disclosure (e.g. Formula I, I-X, 1, or 2, or any one of Compound Nos. 1-8, or pharmaceutically acceptable salt thereof). In some embodiments, the prodrug is a compound of Formula I-X, or a pharmaceutically acceptable salt thereof, wherein D is a residue of a controlled substance listed in Table 1, e.g., any of the opioid or phenolic opioid listed in Table 1. In some embodiments, D is a residue of morphine, oxymorphone, hydromorphone, levorphanol, or oxycodone. In some embodiments, the prodrug can be a compound of Formula 1 or 2 (e.g., any of the Compound Nos. 1-8), or a pharmaceutically acceptable salt thereof. In some embodiments, the pharmaceutical composition can achieve a long acting release of the controlled substance. For example, in some embodiments, the pharmaceutical composition can, after administration, release the controlled substance, or a metabolite thereof, in a subject user over an extended period of time, such as at least 3 days.

In some embodiments, the pharmaceutical composition of the present disclosure is abuse deterrent. As explained herein, the pharmaceutical composition of the present disclosure can reduce the potential of drug abuse. For example, in some embodiments, the pharmaceutical composition can be formulated for injection, such as subcutaneous or intramuscular injection, which can be restricted to hospital use. As this reduces the availability of the formulation to a potential abuser, the likelihood of drug abuse of the controlled substance is also reduced. Further, as the pharmaceutical composition typically releases the controlled substance or a metabolite thereof slowly after administration, the abuser's potential reward of euphoria may not be achieved by simply administering the pharmaceutical composition (e.g., through injection). Moreover, the pharmaceutical composition herein can also be characterized as being resistant towards (e.g., substantially stable under) common abuse conditions. For example, in some embodiments, the pharmaceutical composition is substantially stable under acid- or base-catalyzed hydrolysis conditions, e.g., with a pH of about 1-3 (acid catalyzed) or about 8-9 (base-catalyzed), such as vinegar or baking soda mediated hydrolysis, at a pH of about 2.4 or about 8.3, or a citric acid mediated hydrolysis at a pH of about 1.6. In some embodiments, the pharmaceutical composition can comprise micelles comprising the prodrug of the present disclosure. Without wishing to be bound by theories, as micelles are typically more stable towards acid- or base-catalyzed hydrolysis, the pharmaceutical composition comprising micelles of the prodrug can also be abuse deterrent.

In an exemplary embodiment, the pharmaceutical composition includes from 1 g to 2000 mg of a prodrug disclosed herein, e.g., 1 g to 1 mg, 1 mg to 10 mg, 1 mg to 100 mg, 1 mg to 1000 mg, 1 mg to 1500 mg, or even 1 mg to 2000 mg.

The prodrugs of the present disclosure can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The prodrugs of the present disclosure can also be administered by injection, that is, intravenously, intramuscularly, intracutaneously, subcutaneously, intraduodenally, or intraperitoneally. Also, the prodrugs of the present disclosure described herein can be administered by inhalation, for example, intranasally. Additionally, the prodrugs of the present disclosure can be administered transdermally. The prodrugs of the present disclosure can also be administered by in intraocular, intravaginal, and intrarectal routes including suppositories, insufflation, powders and aerosol formulations. The pharmaceutical compositions described herein can be adapted for oral administration.

For preparing pharmaceutical compositions from the prodrugs of the present disclosure, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of REMINGTON'S PHARMACEUTICAL SCIENCES, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the prodrug of the present disclosure mixed with a filler or binders such as lactose or starches, lubricants such as talc or magnesium stearate, and, optionally, stabilizers. In soft capsules, the prodrugs of the present disclosure may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil carriers such as a vegetable oil, such as *arachis* oil, olive oil, sesame oil or coconut oil, or in a mineral oil such as liquid paraffin; or a mixture of these can also be used for formulating the prodrugs of the present disclosure, for example, for an injectable formulation. In some embodiments, the oil is used as a carrier, and the prodrug is suspended in the oil carrier. In some embodiments, the oil suspensions can contain a thickening agent, such as beeswax, hard paraffin or cetyl alcohol. Sweetening agents can be added to provide a palatable oral preparation, such as glycerol, sorbitol or sucrose. These formulations can also be preserved by the addition of an antioxidant such as ascorbic acid. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The prodrugs of the present disclosure can be delivered transdermally, by a topical route, formulated as applicator sticks, solutions, suspensions, emulsions, gels, creams, ointments, pastes, jellies, paints, powders, and aerosols.

The prodrugs of the present disclosure can also be delivered as microspheres or implants for slow release in the body. For example, microspheres can be administered via intradermal injection of drug-containing microspheres, which slowly release subcutaneously; as biodegradable and injectable gel formulations; or, as microspheres for oral administration. Both transdermal and intradermal routes afford constant delivery for weeks or months.

The prodrugs of the present disclosure can also be delivered as subcutaneous (SC) or intramuscular (IM) injectable in situ depot for slow release in the body. The prodrug can be mixed with organic solvent in the syringe and remains in liquid form. After injection, the prodrug can form an in situ depot, which constantly deliver drug for weeks or months.

The prodrugs of the present disclosure can be provided as a salt which can be formed with many different types of acids, including but not limited to hydrochloric, sulfuric, acetic, lactic, tartaric, malic, succinic, etc. Salts tend to be more soluble in aqueous or other protonic solvents than the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the prodrugs of the present disclosure are useful for parenteral administration, such as intravenous (IV) administration or administration into a body cavity or lumen of an organ. The formulations for administration will commonly comprise a solution of the compound dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the prodrug in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the prodrugs of the present disclosure can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the prodrug into the target cells in vivo.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Prodrugs of the present disclosure may be metabolized by lipases or esterases, When the prodrug is metabolized by lipases or easterases, the ester bond is cleaved and the active controlled substance (e.g., an opioid) is released.

Utilizing the teachings provided herein, an effective dosing regimen can be planned which can involve careful selection of active compounds by considering factors such as compound potency, relative bioavailability, release rate, patient body weight, presence and severity of adverse side effects, preferred mode of administration, and the toxicity profile of the selected agent.

V. Exemplary Embodiments

Showing below are a few exemplary embodiments E1-E11.

1. A compound having the structure of Formula (I), or a pharmaceutically acceptable salts thereof.

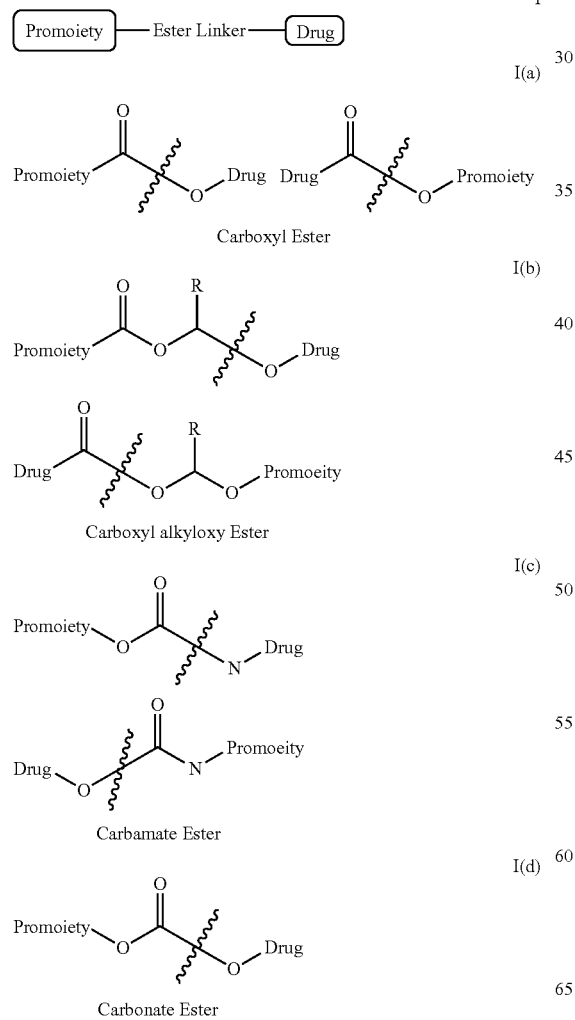

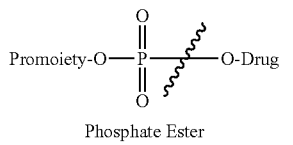

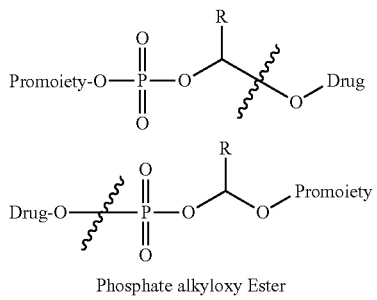

wherein: Ester linker is Formula I(a) as carboxyl ester, Formula I(b) as carboxylakyloxy ester, Formula I(c) cabamate ester, Formula I(d) as carbonate ester, Formula I(e) as phosphate ester, and Formula I(f) as phosphate carboxylalkyloxy ester; Promoiety is selected from a lipid a natural biodegradable polymer and a synthetic polymer; Drug is selected from a Schedule II, III, or IV controlled substance with hydroxyl, secondary amine, or carboxyl acid group in Table 1; and R is selected from hydrogen, alkyl or substituted alkyl group.

2. The compound of embodiment 1, wherein the lipid comprises of saturated or unsaturated, straight chain or branched chain lipid with eight (8) to twenty four (24) carbons; the lipid further comprises of bile acids, squalene, vitamin E and its derivatives such as vitamin E TPGS, cholesterols, and retinoic acids.
3. The compound of embodiment 1, wherein the natural biodegradable polymer comprises of alginate, chitosan, derived cellulose, starch, hyaluronic acid, and dextran; and the synthetic polymer comprises of polyesters, polyethers, polyurethanes, polyphospazines, polycarbonates, and polyesteramide.
4. The compound of embodiment 3, wherein the polyester comprises of polylactic (PLA), polyglycolic (PGA), polycarprolactone (PCL), and their copolymers including polylactic glycolic acid (PLGA); and polyether comprises of polyethylene glycol (PEG) and its derivatives.
5. The compound of embodiment 1, wherein the drug is a morphine, oxymorphone, hydromorphone, and oxycodone.
6. The compound of embodiment 3, wherein the ester linker is carboxyl ester.
7. The compound of embodiment 2, wherein the lipid is straight chain fatty acid with 12-20 carbons.
8. The compound of embodiment 1, wherein the pharmaceutically accepted salt is formed with an acid selected from the group consisting of acetic acid, hydrobromic acid, hydrochloride acid, citric acid, maleic acid, methanesulfonic acid, nitric acid, phosphoric acid, succinic acid, sulfuric acid, and tartaric acid.
9. A pharmaceutical composition comprising a compound of embodiment 1 and a pharmaceutically acceptable excipient.

10. The pharmaceutical composition of embodiment 9 can be injected subcutaneously or intramuscularly for long acting release.
11. A method of resisting opioid drug tampering and abuse comprising administering to a subject in need thereof an effective amount of the compound of one of embodiment 1.

VI. Examples

Example 1—Synthesis of Oxymorphone Ester Prodrugs

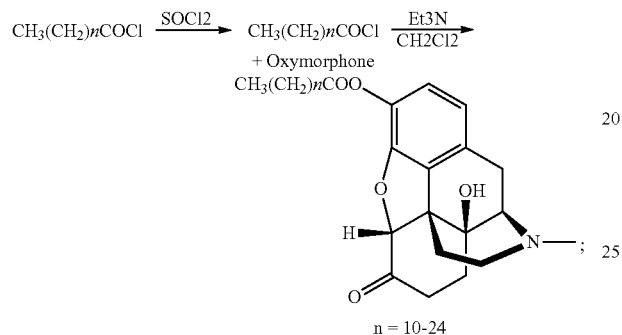

n = 10-24

Exemplary procedure for preparing oxymorphone palmitic (n=14) esters. Fatty acid (palmitic acid) and sulfonyl chloride (>10 mol eq) were added in a dry round bottom flask. The mixture was refluxed for 2 hours at 85° C. in an oil bath. The liquid sulfonyl chloride was removed under vacuum using a rotavap and further using an oil pump. Anhydrous $CH_2Cl_2$ was added into the mixture. The added solvent was then removed under vacuum using a rotavap and further using an oil pump. The steps of adding and removing of anhydrous $CH_2CH_2$ were repeated three times to ensure the residual sulfonyl chloride was completely removed. The obtained light yellow crystal was used for next reaction without further purification.

Oxymorphone chloride salt (1.0 mol eq) and triethylamine (4.0 mol eq) were dissolved in anhydrous $CH_2Cl_2$ in a round bottom flask. The flask was kept in an ice water bath. Fatty acid chloride (palmitic acid chloride) (1.1 mol eq) prepared above was added into the mixture. The mixture was stirred overnight. The mixture was washed with 0.1 N citric acid (2 times) and with water (1 time). The organic phase was collected, and dried with anhydrous $K_2SO_4$. The organic solvent was removed using a rotavap. The obtained mixture was purified with silica chromatography using $CH_2Cl_2$:MeOH=20:1.

Following the procedure above, oxymorphone esters with n=10, 14, 18, and 22 were synthesized. The product obtained was a light yellow oil (or white powder) and the reaction yield is generally >80%.

Characterization of products.

Compound 1. Oxymorphone dodecanate (n is 10). MS (m/z): 484.3. $^1$H NMR (300 MHz, $CDCl_3$) δ 6.83 (1H, d), 6.69 (1H, d), 4.68 (1H, s), 3.19 (1H, d), 3.00 (2H, m), 2.0-2.7 (10H, m), 1.6-1.8 (5H, m), 1.0-1.5 (16H, m), 0.87 (3H, t). Compound 1 was obtained as a light yellow oil.

Compound 2. Oxymorphone hexadecanate (n is 14). MS (m/z): 540.3. $^1$H NMR (300 MHz, $CDCl_3$) δ 6.84 (1H, d), 6.69 (1H, d), 4.68 (1H, s), 2.9-3.4 (3H, m), 2.0-2.6 (10H, m), 1.6-1.8 (5H, m), 1.0-1.5 (24H, m), 0.87 (3H, t). Compound 2 was obtained as a white wax.

Compound 3. Oxymorphone eicosanate (n is 18). MS (m/z): 596.4. $^1$H NMR (300 MHz, $CDCl_3$) δ 6.84 (1H, d), 6.69 (1H, d), 4.68 (1H, s), 2.9-3.4 (2H, m), 1.9-2.7 (10H, m), 1.6-1.8 (6H, m), 1.0-1.6 (32H, m), 0.87 (3H, t). Compound 3 was obtained as a white powder.

Compound 4. Oxymorphone tetracosanate (n is 22). MS (m/z): 652.4. $^1$H NMR (300 MHz, $CDCl_3$) δ 6.84 (1H, d), 6.69 (1H, d), 4.69 (1H, s), 3.30 (1H, s), 3.08 (2H, m), 2.0-2.8 (10H, m), 1.6-2.0 (5H, m), 1.0-1.5 (40H, m), 0.87 (3H, t). Compound 4 was obtained as an off-white powder.

Example 2—Synthesis of Hydromorphone Ester Prodrugs

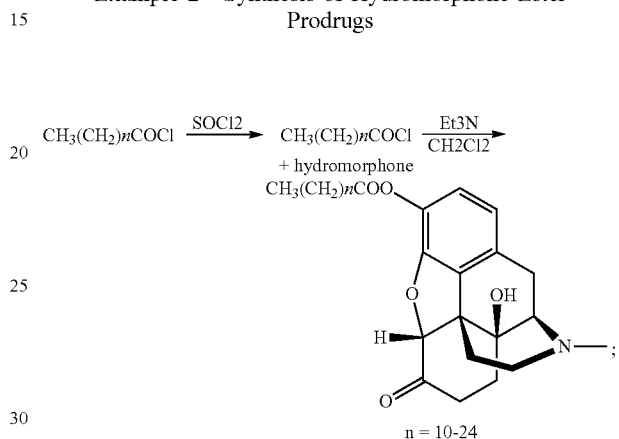

n = 10-24

Following the procedure described in Example 1, using hydromorphone chloride salt instead, hydromorphone esters with n=10, 14, 18, and 22 were prepared.

Characterization of products.

Compound 5. Hydromorphone dodecanate (n is 10). MS (m/z): 468.3. $^1$H NMR (300 MHz, $CDCl_3$) δ 6.82 (1H, d), 6.68 (1H, d), 4.67 (1H, s), 3.24 (1H, s), 3.05 (1H, s), 2.0-2.6 (11H, m), 1.6-1.8 (4H, m), 1.0-1.5 (18H, m), 0.87 (3H, t). Compound 5 was obtained as a light yellow oil.

Compound 6. Hydromorphone hexadecanate (n is 14). MS (m/z): 524.3. $^1$H NMR (300 MHz, $CDCl_3$) δ 6.83 (1H, d), 6.68 (1H, d), 4.68 (1H, s), 3.66 (1H, s), 2.9-3.4 (2H, m), 1.9-2.6 (12H, m), 1.6-1.8 (4H, m), 1.0-1.5 (24H, m), 0.87 (3H, t). Compound 6 was obtained as a light yellow oil.

Compound 7. Hydromorphone eicosanate (n is 18). MS (m/z): 580.4. $^1$H NMR (300 MHz, $CDCl_3$) δ 6.82 (1H, d), 6.68 (1H, d), 4.67 (1H, s), 3.65 (1H, m), 2.9-3.4 (4H, m), 1.9-2.6 (10H, m), 1.6-1.8 (4H, m), 1.0-1.6 (32H, m), 0.87 (3H, t). Compound 7 was obtained as a white wax.

Compound 8. Hydromorphone tetracosanate (n is 22). MS (m/z): 636.4. $^1$H NMR (300 MHz, $CDCl_3$) δ 6.84 (1H, d), 6.69 (1H, d), 4.69 (1H, s), 3.27 (1H, s), 3.08 (1H, d), 2.0-2.8 (11H, m), 1.6-2.0 (4H, m), 1.0-1.5 (42H, m), 0.87 (3H, t). Compound 8 was obtained as an off-white powder.

Example 3—Stability Study Under Tampering Conditions

The prodrugs are subjected to common tampering condition, including 1.0M baking soda (pH=8.3), vinegar (5% acetic acid, pH=2.5), and Vodka (40% alcohol) at 80° C., and chlorine and hydrogen peroxide at 25° C. The final incubation mixture contains 10 μM test compound in a final volume of 0.5 mL tampering medium. The prodrug is added to initiate the incubation. At 0, 30, and 60 minutes, 0.05 mL aliquots is removed from the incubation mixtures and quenched with 0.15 mL of methanol and placed on ice. Aliquot is taken out for analysis. The concentration of both prodrug and parent drug is analyzed by LC-MS/MS to compare the stability of prodrugs.

Example 4—Stability Study in Human Carboxyl Esterase and Lipase

The prodrugs are tested in recombinant human carboxyl esterase mixture containing human recombinant carboxylesterase 1b, human recombinant carboxylesterase 1c, and human recombinant carboxylesterase 2. The prodrugs are also tested in recombinant human pancreatic lipase. The hydrolysis rate in carboxyl esterase and lipase provide a ranking of the stability of the prodrugs in biological conditions.

The final incubation mixture contains 1 µM test compound and 0.1 mg/mL human recombinant carboxylesterase mixture or lipase in a final volume of 1.0 mL 0.1M potassium phosphate buffer (pH=6.0). The final percentage of DMSO in the incubation is 1.0% or less to prevent inhibition of enzymatic activity. Following a pre-incubation at 37° C., test article is added to initiate the reaction. Aliquots of 0.02 mL is removed from the incubation at 0, 30 and 60 minutes and quenched by adding 0.18 mL of freshly prepared 6N guanidinium hydrochloride solution in water containing 0.01% (v/v) phosphoric acid. The mixture is then centrifuged at 7500 g for 10 minutes at 4° C. and the supernatant is analyzed using LC-MS/MS. The percentage remaining of the prodrug and the formation of parent drug is recorded.

Example 5—Stability Study in Human Plasma

Selected prodrugs are tested in human plasma to evaluate their stability. The final incubation mixture contains 1 µM test compound in a final volume of 1.0 mL human plasma. The final percentage of DMSO in the incubation is 1.0% or less to prevent inhibition of enzymatic activity. Following a pre-incubation at 37° C., test article is added to initiate the reaction. Aliquots of 0.02 mL is removed from the incubation at 0, 30 and 60 minutes and quenched by adding 0.18 mL of freshly prepared 6N guanidinium hydrochloride solution in water containing 0.01% (v/v) phosphoric acid. The mixture is then centrifuged at 7500 g for 10 minutes at 4° C. and the supernatant is analyzed using LC-MS/MS. The percentage remaining of the prodrug and the formation of parent drug are recorded.

Example 6—Pharmacokinetic Study in Rats

General Procure: The formulations of opioid ester prodrugs are prepared to provide 180 mg/ml suspension by adding 1.8 g of prodrug to a 50 ml glass vial. To the solids is added 30 ml of injection vehicle (2-3% sodium CMC, 0.2% polysorbate 20 in phosphate buffered saline (PBS) pH 7). The resulting mixture is sonicated for 10 min and left standing. The contents of the vial is then shaken until a uniform, clump-free suspension is obtained prior to dosing.

Twelve male Male Sprague-Dawley rats with a body weight approximately 250 g are used in the study. A single intramuscular injection of ester prodrug (180 mg) is administered to rats. Blood samples is collected at 0 (pretreatment) 0.5, 1, 2, 4, 8, 12 and 24 days after administration. Blood is collected with commercially available plastic tubes containing a clot activator. Within 10 min of collection, blood is centrifugation at 2.500 g for 10 min. Plasma is separated and frozen at −18° C. until analyzed by LC-MS/MS. Both prodrug and its corresponding parent drug are analyzed. The pharmacokinetic parameters (AUC, Tmax, Cmax, T1/2, etc) of the test articles are compared to compare the performance of prodrugs to their parent drugs.

Pharmacokinetic Studies for Compounds 2, 3, and 7. Pharmacokinetic studies were conducted for three compounds (Compounds 2, 3 and 7) in rats. The formulations were prepared either in sesame oil (Compound 2, 100 mg eq/mL) or aqueous suspension (Compounds 3 and 7, 100 mg eq/mL and 60 mg eq/mL, respectively). The dosage "eq" refers to the equivalent dosing amount of the respective parent drug, e.g., oxymorphone or hydromorphone in this Example. The sesame oil formulation contains 1.2% benzyl alcohol. The suspension formulation was prepared in PBS buffer containing 2% CMC and 0.2% Tween 80. The particle sizes of the testing compounds in suspension were kept under 10 micron. Both oil and suspension formulations were sterilized by electronic beam before administered to Sprague-Dawley rats.

Twelve Male Sprague-Dawley rats with body weight of approximately 250 gram were randomly divided into three groups. The rats were housed in cages for at least 5 days prior to entering the study and had free access to standard pellets and water during the period. The formulations (0.05 mL) were administered to rats by intra muscular injection via hind leg. Blood (0.10 mL) was sampled by individual tail vein puncture at the following time points: 0.5, 2, 8 hours, 1, 3, 6, 13, 27 days post-dose. Blood was collected into $K_2EDTA$ coated tubes and centrifuged at 4° C. at 2000 g in for 10 min to obtain plasma. Plasma (0.05 mL) was immediately quenched with 100 uL methanol/acetonitrile (1:1) containing 50 ng/mL ISTD (Terfenadine and Buspirone). The mixture was vortexed for 1 min and centrifuged at 4000 rpm for 15 min. Supernatant was diluted 2 fold with 0.1% FA in water for injection. Both prodrug and the drug were analyzed using LC-MS/MS on AB Sciex API 5500. The pharmacokinetic parameters were calculated and reported as following.

Figure 1B:
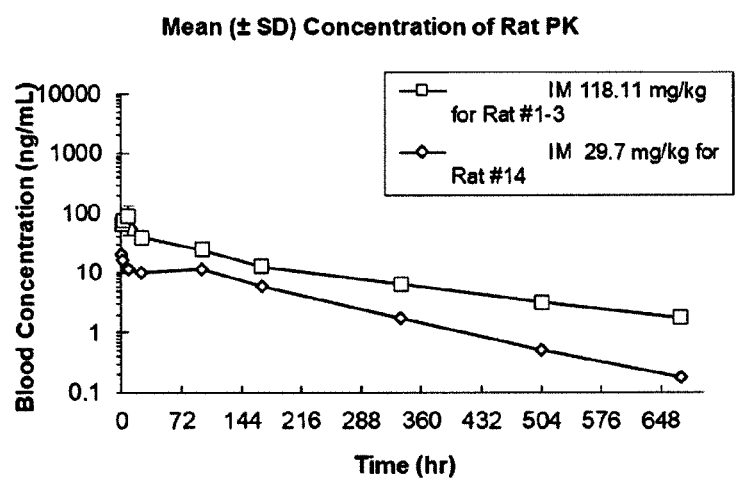

Tables 2A and 2B summarize the pharmacokinetic data observed and/or calculated for the PK study for Compound 2. Table 2A shows the PK profile of the prodrug Compound 2 and Table 2B shows the PK profile of parent drug oxymorphone observed from intramuscular injection of Compound 2 in this study. See also FIGS. 1A and 1B for PK graphs.

TABLE 2A

Plasma Concentration Profile of Compound 2

| | $t_{1/2}$ (hr) | $t_{max}$ (hr) | $C_{max}$ (ng/mL) | $AUC_{last}$ (hr*ng/mL) | $AUC_{Inf}$ (hr*ng/mL) | AUC Extr (%) | $MRT_{Inf}$ (hr) | $AUC_{Inf}/D$ (hr*kg*ng/mL/mg) |
|---|---|---|---|---|---|---|---|---|
| Compound 2 IM administration; 118.11 mg/kg for Rat #1-3 | | | | | | | | |
| Mean | 130 | 3.50 | 1.62 | 51.3 | 101 | 39.8 | 156 | 0.857 |
| SD | 42 | 3.97 | 0.53 | 7.3 | 51 | 28.9 | 86 | 0.435 |
| CV (%) | 32.8 | 113 | 32.8 | 14.3 | 50.7 | 72.7 | 55.3 | 50.7 |

TABLE 2A-continued

Plasma Concentration Profile of Compound 2

|  | $t_{1/2}$ (hr) | $t_{max}$ (hr) | $C_{max}$ (ng/mL) | $AUC_{last}$ (hr*ng/mL) | $AUC_{Inf}$ (hr*ng/mL) | AUC Extr (%) | $MRT_{Inf}$ (hr) | $AUC_{Inf}$/D (hr*kg*ng/mL/mg) |
|---|---|---|---|---|---|---|---|---|
| Compound 2 IM administration; 29.7 mg/kg for Rat #14 ||||||||
| Mean | 76 | 2.00 | 0.54 | 17.4 | 30.3 | 42.6 | 108 | 1.02 |
| SD | NA | NA | NA | NA | NA | NA | NA | NA |
| CV (%) | NA | NA | NA | NA | NA | NA | NA | NA |

TABLE 2B

Plasma Concentration Profile of Oxymorphone

|  | $t_{1/2}$ (hr) | $t_{max}$ (hr) | $C_{max}$ (ng/mL) | $AUC_{last}$ (hr*ng/mL) | $AUC_{Inf}$ (hr*ng/mL) | AUC Extr (%) | $MRT_{Inf}$ (hr) | $C_{max}$ Ratio (Parent/Pro) | $AUC_{last}$ Ratio (Parent/Pro) |
|---|---|---|---|---|---|---|---|---|---|
| Compound 2 IM administration; 118.11 mg/kg for Rat #1-3 |||||||||
| Mean | 184 | 3.50 | 95.3 | 8219 | 8711 | 5.71 | 196 | 63.7 | 161 |
| SD | 42 | 3.97 | 38.5 | 1012 | 964 | 2.68 | 34 | 29.1 | 13 |
| CV (%) | 22.6 | 113 | 40.4 | 12.3 | 11.1 | 47.0 | 17.4 | 45.7 | 8.13 |
| Compound 2 IM administration; 29.7 mg/kg for Rat #14 |||||||||
| Mean | 102 | 0.50 | 21.0 | 2612 | 2638 | 0.99 | 147 | 21.0 | 151 |
| SD | NA | NA | NA | NA | NA | NA | NA | NA | NA |
| CV (%) | NA | NA | NA | NA | NA | NA | NA | NA | NA |

Figure 2A:
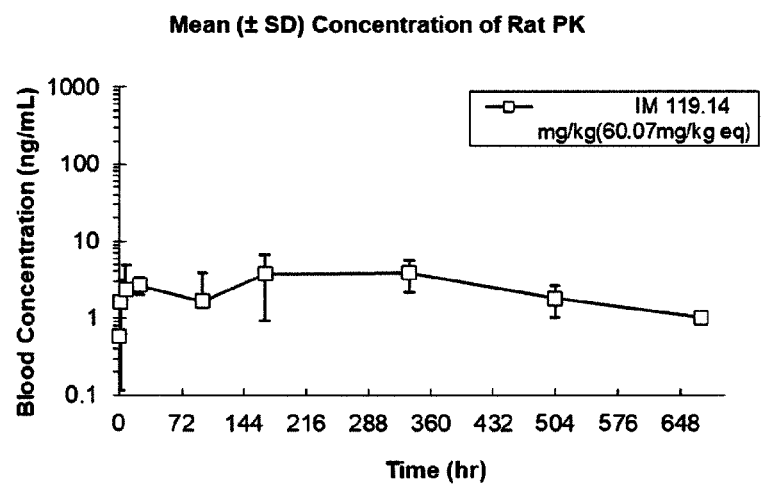
FIGS. 2A and 2B present graphs showing the plasma concentration profile of Compound 3 and oxymorphone, respectively, over the course of about 30 days post administration of Compound 3 in a rat PK study. The graphs were based on data points from mean (±Standard Deviation).
Figure 2B:
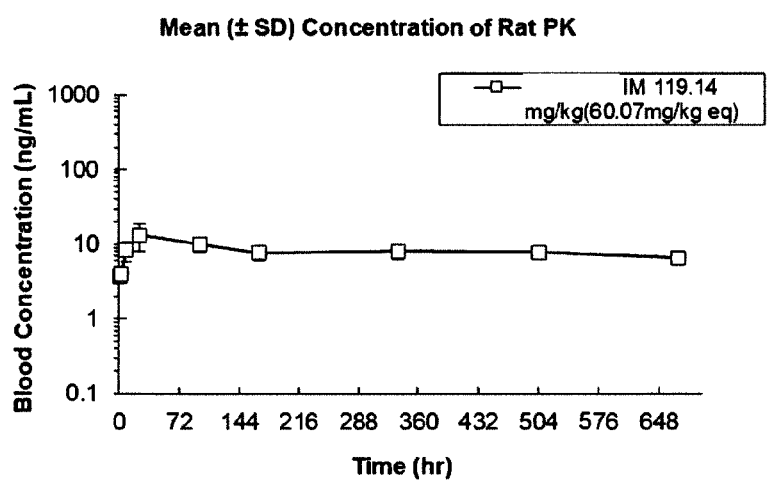

Tables 3A and 3B summarize the pharmacokinetic data observed and/or calculated for the PK study for Compound 3. Table 3A shows the PK profile of the prodrug Compound 3 and Table 3B shows the PK profile of the parent drug oxymorphone from intramuscular injection of Compound 3 in this study. See also FIGS. 2A and 2B for PK graphs.

TABLE 3A

Plasma Concentration Profile of Compound 3.
Compound 3 IM administration; 119.14 mg/kg; N = 4

|  | $t_{1/2}$ (hr) | $t_{max}$ (hr) | $C_{max}$ (ng/mL) | $AUC_{last}$ (hr*ng/mL) | $AUC_{Inf}$ (hr*ng/mL) | AUC Extr (%) | $MRT_{Inf}$ (hr) | $AUC_{Inf}$/D (hr*kg*ng/mL/mg) |
|---|---|---|---|---|---|---|---|---|
| Mean | 263 | 212 | 4.79 | 1711 | 2355 | 29.9 | 484 | 19.8 |
| SD | 97 | 157 | 2.06 | 1132 | 986 | 22.9 | 128 | 8.3 |
| CV (%) | 36.9 | 74.2 | 43.1 | 66.1 | 41.9 | 76.7 | 26.5 | 41.9 |

TABLE 3B

Plasma Concentration Profile of Oxymorphone.
Compound 3 IM administration; 119.14 mg/kg, N = 4

|  | $t_{1/2}$ (hr) | $t_{max}$ (hr) | $C_{max}$ (ng/mL) | $AUC_{last}$ (hr*ng/mL) | $AUC_{Inf}$ (hr*ng/mL) | AUC Extr (%) | $MRT_{Inf}$ (hr) | $C_{max}$ Ratio (Parent/Pro) | $AUC_{last}$ Ratio (Parent/Pro) |
|---|---|---|---|---|---|---|---|---|---|
| Mean | 1320 | 42.0 | 13.5 | 5598 | 18261 | 63.7 | 1917 | 3.22 | 4.44 |
| SD | 923 | 36.0 | 5.1 | 983 | 7777 | 17.8 | 1366 | 1.82 | 2.71 |
| CV (%) | 69.9 | 85.7 | 37.5 | 17.6 | 42.6 | 27.9 | 71.3 | 56.4 | 61.1 |

Figure 3A:
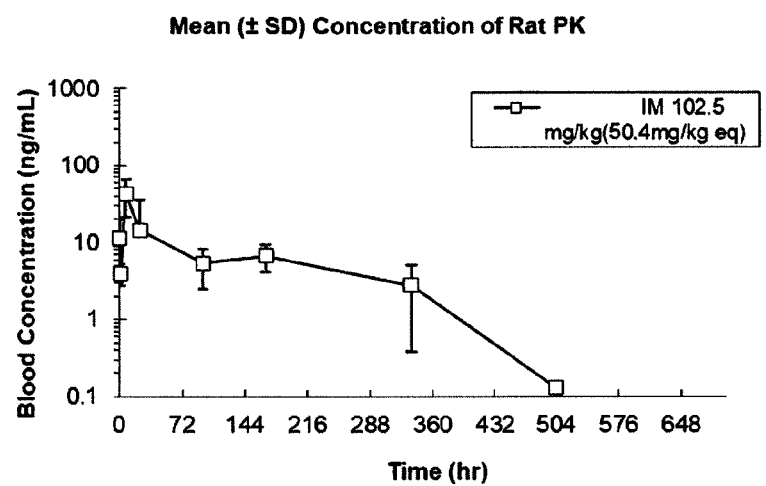
FIGS. 3A and 3B present graphs showing the plasma concentration profile of Compound 7 and hydromorphone, respectively, over the course of about 30 days post administration of Compound 7 in a rat PK study. The graphs were based on data points from mean (±Standard Deviation).
Figure 3B:
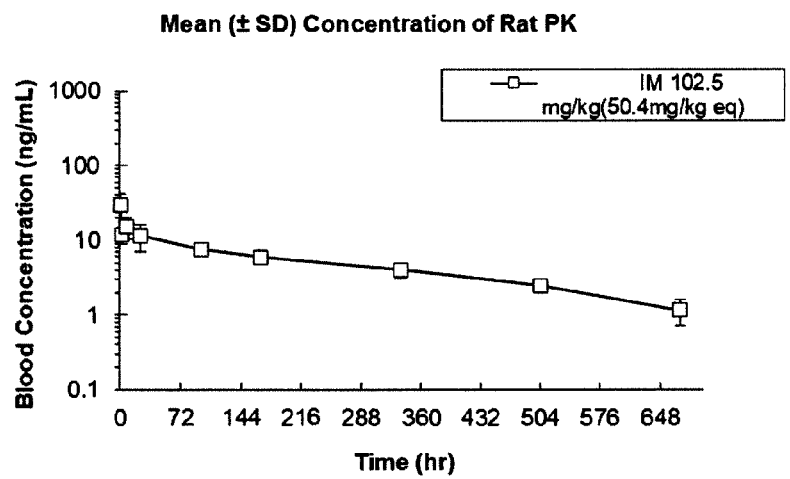

Tables 4A and 4B summarize the pharmacokinetic data observed and/or calculated for the PK study for Compound 7. Table 4A shows the PK profile of the prodrug Compound 7 and Table 4B shows the PK profile of the parent drug hydromorphone from intramuscular injection of Compound 7 in this study. See also FIGS. 3A and 3B for PK graphs.

TABLE 4A

Plasma Concentration Profile of Compound 7.
Compound 7 IM administration; 102.5 mg/kg; N = 4

|  | $t_{1/2}$ (hr) | $t_{max}$ (hr) | $C_{max}$ (ng/mL) | $AUC_{last}$ (hr*ng/mL) | $AUC_{Inf}$ (hr*ng/mL) | AUC Extr (%) | $MRT_{Inf}$ (hr) | $AUC_{Inf}/D$ (hr*kg*ng/mL/mg) |
|---|---|---|---|---|---|---|---|---|
| Mean | 64.4 | 6.13 | 45.6 | 2755 | 2846 | 4.36 | 138 | 27.8 |
| SD | 30.2 | 3.75 | 17.3 | 1716 | 1667 | 6.66 | 43 | 16.3 |
| CV (%) | 46.8 | 61.2 | 38.0 | 62.3 | 58.6 | 153 | 31.3 | 58.6 |

TABLE 4B

Plasma Concentration Profile of Hydromorphone.
Compound 7 IM administration; 102.5 mg/kg; N = 4

|  | $t_{1/2}$ (hr) | $t_{max}$ (hr) | $C_{max}$ (ng/mL) | $AUC_{last}$ (hr*ng/mL) | $AUC_{Inf}$ (hr*ng/mL) | AUC Extr (%) | $MRT_{Inf}$ (hr) | $C_{max}$ Ratio (Parent/Pro) | $AUC_{last}$ Ratio (Parent/Pro) |
|---|---|---|---|---|---|---|---|---|---|
| Mean | 233 | 0.500 | 29.5 | 3201 | 3657 | 12.0 | 329 | 0.757 | 1.56 |
| SD | 153 | 0.000 | 12.2 | 300 | 253 | 11.3 | 144 | 0.444 | 0.883 |
| CV (%) | 65.9 | 0.000 | 41.2 | 9.38 | 6.91 | 93.6 | 43.6 | 58.6 | 56.7 |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound of Formula 1 or a pharmaceutically acceptable salt thereof,

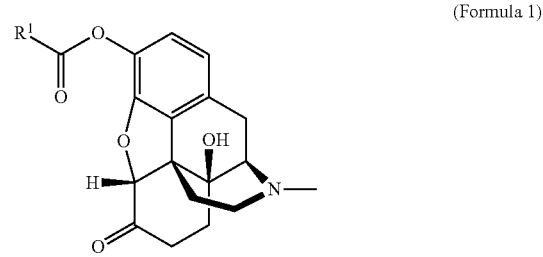

(Formula 1)

wherein $R^1$ is $R^{10}$, $-OR^{10}$, or $-NHR^{10}$, wherein $R^{10}$ is an optionally substituted straight or branched alkyl, alkenyl, or alkynyl chain having a total number of 7-30 carbons.

2. The compound of claim 1 or pharmaceutically acceptable salt thereof, wherein $R^{10}$ is an unsubstituted straight or branched alkyl chain having 7-30 carbons.

3. The compound of claim 1, or a pharmaceutically acceptable salt thereof, wherein $R^1$ is an unsubstituted straight alkyl chain having a formula of $CH_3(CH_2)_n-$, wherein n is an integer of 8-24.

4. The compound of claim 3 or pharmaceutically acceptable salt thereof, wherein $R^1$ is selected from $CH_3(CH_2)_{10}-$, $CH_3(CH_2)_{12}-$, $CH_3(CH_2)_{14}-$, and $CH_3(CH_2)_{16}-$.

5. The compound of claim 1 or pharmaceutically acceptable salt thereof, wherein the alkyl, alkenyl, or alkynyl chain is optionally substituted with one or more groups independently selected from halogen, optionally substituted $C_{1-6}$ alkyl, optionally substituted $C_{1-6}$ heteroalkyl with 1 or 2 heteroatoms independently selected from oxygen and nitrogen, optionally substituted $C_{2-6}$ alkenyl, optionally substituted $C_{2-6}$ alkynyl, optionally substituted $C_{3-6}$ cycloalkyl, optionally substituted $C_{6-14}$ aryl, optionally substituted 5-8 membered heterocycloalkyl, optionally substituted 5-10 membered heteroaryl, short peptides, —$NR^{100}R^{101}$, —C(=O)$NR^{100}R^{101}$, —$COOR^{102}$, and —$OR^{102}$, wherein $R^{100}$, $R^{101}$, and $R^{102}$ are each independently hydrogen, optionally substituted $C_{1-6}$ alkyl, optionally substituted $C_{1-6}$ heteroalkyl with 1 or 2 heteroatoms independently selected from oxygen and nitrogen, optionally substituted $C_{3-6}$ cycloalkyl, optionally substituted $C_{6-14}$ aryl, optionally substituted 5-8 membered heterocycloalkyl, optionally substituted 5-10 membered heteroaryl, wherein each of the optionally substituted groups is independently optionally substituted with one or more substituents selected from oxo, halogen, hydroxyl, $NH_2$, —$NH(C_{1-4}$ alkyl), —$N(C_{1-4}$ alkyl)($C_{1-4}$ alkyl), $C_{1-4}$ alkyl optionally substituted with 1-3 fluorine, $C_{1-4}$ alkoxy optionally substituted with 1-3 fluorine, $C_{2-4}$ alkenyl, $C_{2-4}$ alkynyl, $C_{3-6}$ cycloalkyl optionally substituted with 1-3 fluorine or 1-2 $C_{1-4}$ alkyl, and $C_{3-6}$ cycloalkoxy optionally substituted with 1-3 fluorine or 1-2 $C_{1-4}$ alkyl, wherein the short peptides are mono-, di-, tri-, or tetra-peptides derived from alpha-amino acids selected from alanine, isoleucine, leucine, methionine, valine, phenylalanine, tryptophan, tyrosine, asparagine, cysteine, glutamine, serine, threonine, aspartic acid, glutamic acid, arginine, histidine, lysine, glycine, and proline.

6. A pharmaceutical composition comprising the compound of claim 1 or pharmaceutically acceptable salt thereof and a pharmaceutically acceptable excipient or carrier.

7. A method of treating pain in a subject in need thereof, the method comprising administering to the subject a therapeutically effective amount of the compound of claim 1 or pharmaceutically acceptable salt thereof.

8. The method of claim 7, wherein the administration is via the subcutaneous or intramuscular route.

9. The compound of claim 3 or pharmaceutically acceptable salt thereof, wherein $R^1$ is $CH_3(CH_2)_{10}$—.

10. The compound of claim 3 or pharmaceutically acceptable salt thereof, wherein $R^1$ is $CH_3(CH_2)_{12}$—.

11. The compound of claim 3 or pharmaceutically acceptable salt thereof, wherein $R^1$ is $CH_3(CH_2)_{14}$—.

12. The compound of claim 3 or pharmaceutically acceptable salt thereof, wherein $R^1$ is $CH_3(CH_2)_{16}$—.

13. A method of treating pain in a subject in need thereof, the method comprising administering to the subject a therapeutically effective amount of the compound of claim 2 or pharmaceutically acceptable salt thereof.

14. The method of claim 13, wherein the administration is via the subcutaneous or intramuscular route.

15. A method of treating pain in a subject in need thereof, the method comprising administering to the subject a therapeutically effective amount of the compound of claim 3 or pharmaceutically acceptable salt thereof.

16. The method of claim 15, wherein the administration is via the subcutaneous or intramuscular route.

17. A method of treating pain in a subject in need thereof, the method comprising administering to the subject a therapeutically effective amount of the compound of claim 4 or pharmaceutically acceptable salt thereof.

18. The method of claim 17, wherein the administration is via the subcutaneous or intramuscular route.

19. A pharmaceutical composition comprising the compound of claim 2 or pharmaceutically acceptable salt thereof and a pharmaceutically acceptable excipient or carrier.

20. A pharmaceutical composition comprising the compound of claim 3 or pharmaceutically acceptable salt thereof and a pharmaceutically acceptable excipient or carrier.

21. A pharmaceutical composition comprising the compound of claim 4 or pharmaceutically acceptable salt thereof and a pharmaceutically acceptable excipient or carrier.

* * * * *